US008125627B2

(12) United States Patent
Dottery et al.

(10) Patent No.: US 8,125,627 B2
(45) Date of Patent: Feb. 28, 2012

(54) LASER SPECTROSCOPY SYSTEM

(75) Inventors: Ed Dottery, Palm Harbor, FL (US); Rob Waterbury, Palm Harbor, FL (US); Chris Stefano, Dunedin, FL (US); Roy Walters, Enterprise, FL (US); Jeremy Rose, Largo, FL (US); Frank Vilardi, Largo, FL (US)

(73) Assignee: Alakai Defense Systems, Inc., Largo, FL (US)

( * ) Notice: Subject to any disclaimer, the term of this patent is extended or adjusted under 35 U.S.C. 154(b) by 218 days.

(21) Appl. No.: 12/597,761

(22) PCT Filed: Apr. 28, 2008

(86) PCT No.: PCT/US2008/061809
§ 371 (c)(1),
(2), (4) Date: Dec. 9, 2009

(87) PCT Pub. No.: WO2009/011954
PCT Pub. Date: Jan. 22, 2009

(65) Prior Publication Data
US 2010/0085567 A1    Apr. 8, 2010

Related U.S. Application Data

(60) Provisional application No. 60/914,658, filed on Apr. 27, 2007.

(51) Int. Cl.
*G01N 21/00* (2006.01)

(52) U.S. Cl. .......................................... 356/73; 356/301
(58) Field of Classification Search .............. 356/72–73, 356/301, 318
See application file for complete search history.

(56) References Cited

U.S. PATENT DOCUMENTS 4,780,608 A * 10/1988 Cross et al. ................... 250/281
6,204,500 B1    3/2001 Whitehouse et al.

OTHER PUBLICATIONS

Jesus Anzano et al., Atomic Spectroscopy Direct Determination of Aluminum in Archaeological Clays by Laser-Induced Breakdown Spectroscopy, Analytical Letters, 38: 1957-1965, 2005 copyright Taylor & Francis, Inc.

(Continued)

*Primary Examiner* — Tarifur Chowdhury
*Assistant Examiner* — Abdullahi Nur
(74) *Attorney, Agent, or Firm* — Christopher Paradies; Fowler White Boggs P.A.

(57) ABSTRACT

A spectroscopy system including first and second lasers. The first laser is triggered to induce a plasma, such as on a surface of a target at a stand-off distance from the target. The second laser stimulates amplified emissions from the plasma detected by one or more spectroscopes. The gain induced by the second laser detects traces of explosives and other substances on surfaces at stand-off distances. The spectroscopy systems use the same telescopic optics to collect emissions from the detection surface and activated at or just before the peak emission intensity useful for detecting element signatures and intensity ratios from the trace elements in the plasma.

22 Claims, 15 Drawing Sheets

OTHER PUBLICATIONS

D. Mukherjee et al., Quantitative laser-induced breakdown spectroscopy for aerosols via internal calibration: Application to the oxidative coating of aluminum nanoparticles, Journal of Aerosol Science, vol. 37, Issue 6, Jun. 2006, pp. 677-696, copyright 2005 Elsevier 16 pages.

S.K. Sharma et al., Spectrochim, Acta part A: Mol. Biomol. Spectrosc (2007), doi: 10.1016/j.saa.2007.06.045. 10 pages.

John Scaffidi et al., Emission Enhancement Mechanisms in Dual-Pulse LIBS, Jan. 1, 2006 / Analytical Chemistry, 8 pages.

Dennis K. Killinger et al., Enhancement of Nd:YAG LIBS emission of a remote target using a simultaneous CO2 laser pulse, copyright 2007 Optical Society of America, 11 pages.

M. Kuzuya et al., Quantitative analysis of ceramics by laser-induced breakdown spectroscopy, Spectrochimica Acta Part-B Atomic Spectroscopy 58 (5): 957-965 May 30, 2003, abstract only, 1 page.

C. Lopez-Moreno et al., Stand-off analysis of moving targets using laser-induced breakdown spectroscopy, Journal of Analytical Atomic Spectrometry 22 (1): 84-87 2007, abstract only, 1 page.

P. Yaroshchyk et al., A semi-quantitative standard-less analysis method for laser-induced breakdown spectroscopy, Spectrochimica Acta Part-B Atomic Spectroscopy 61 (2): 200-209 Feb. 2006, abstract only, 1 page.

C. Gautier et al., Study of the double-pulse setup with an orthogonal beam geometry for laser-induced breakdown spectroscopy, Spectrochimica Acta Part-B Atomic Spectroscopy 59 (7): 975-986 Jul. 30, 2004, abstract only, 1 page.

F.C. Delucia et al., Laser-induced breakdown spectroscopy (LIBS): A promising versatile chemical sensor technology for hazardous material detection, IEEE Sensors Journal 5 (4) 681-689 Aug. 2005, abstract only, 1 page.

M. Corsi et al., Three-dimentional analysis of laser induced plasmas in single and double pulse configuration, Spectrochimica Acta Part-B Atomic Spectroscopy 59 (5): 723-235 May 21, 2004, abstract only, 1 page.

Sir Johon Townsend, Electricity in Gases, 1915 Oxford University Press, London.

Code of Federal Regulations, Title 21, vol. 8, 23 pages.

\* cited by examiner

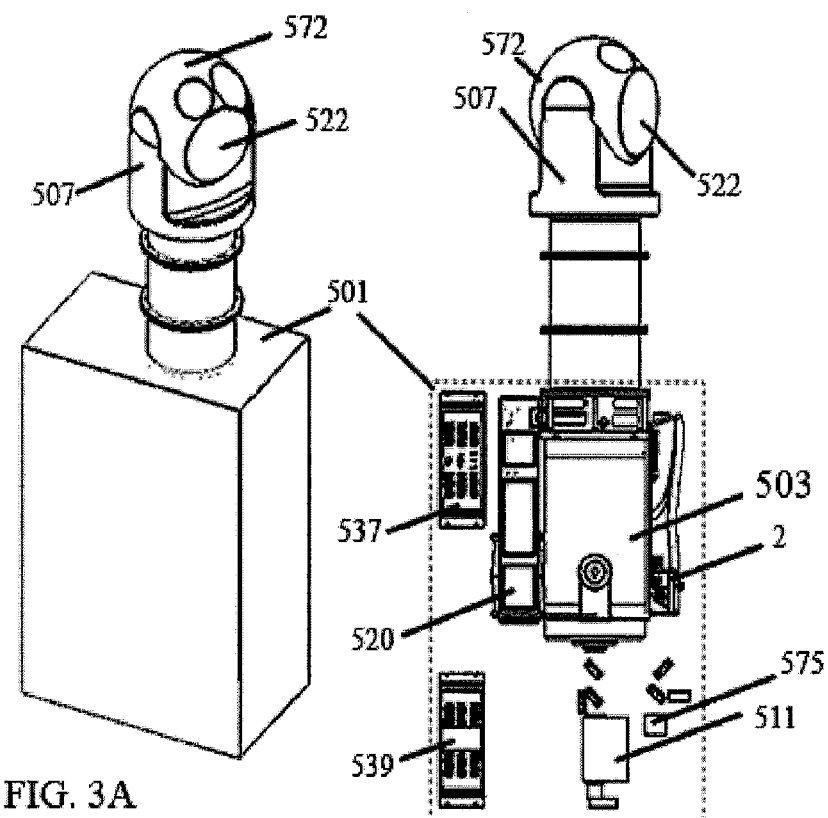
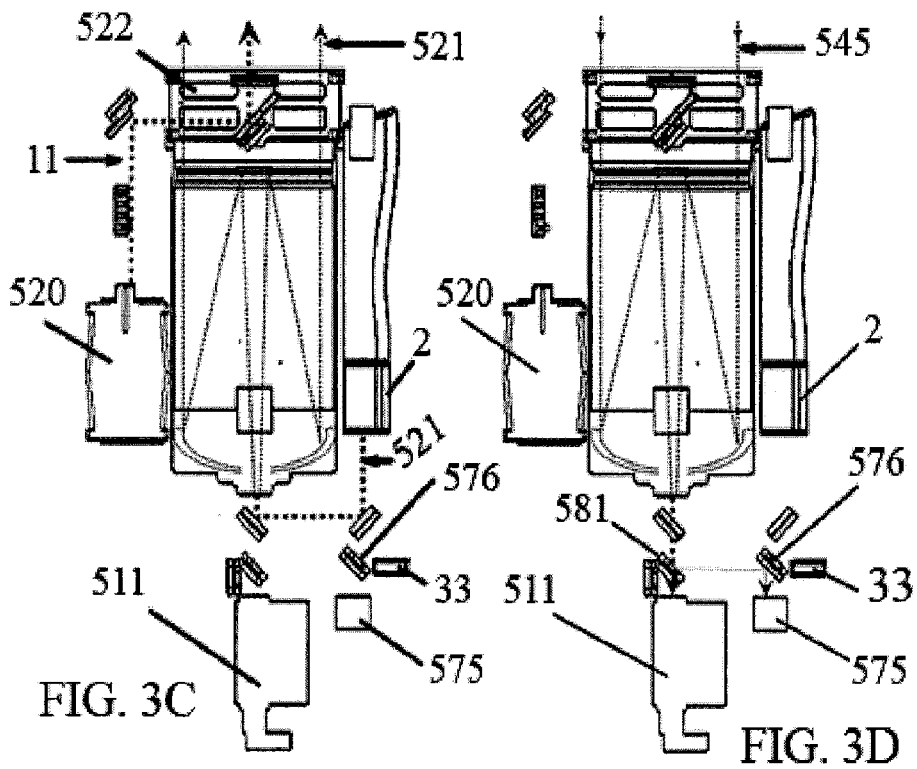
FIG. 3A
FIG. 3B
FIG. 3C
FIG. 3D

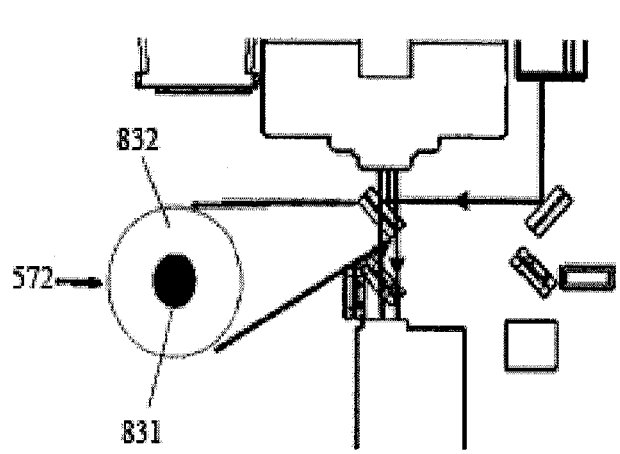
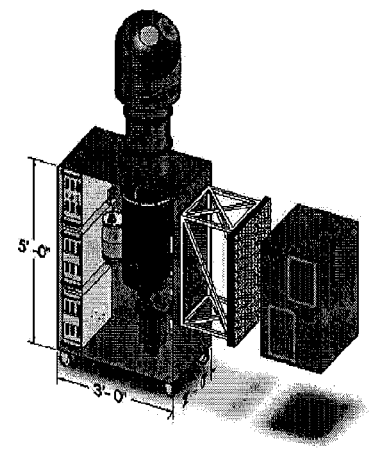
FIG. 3E  FIG. 3F
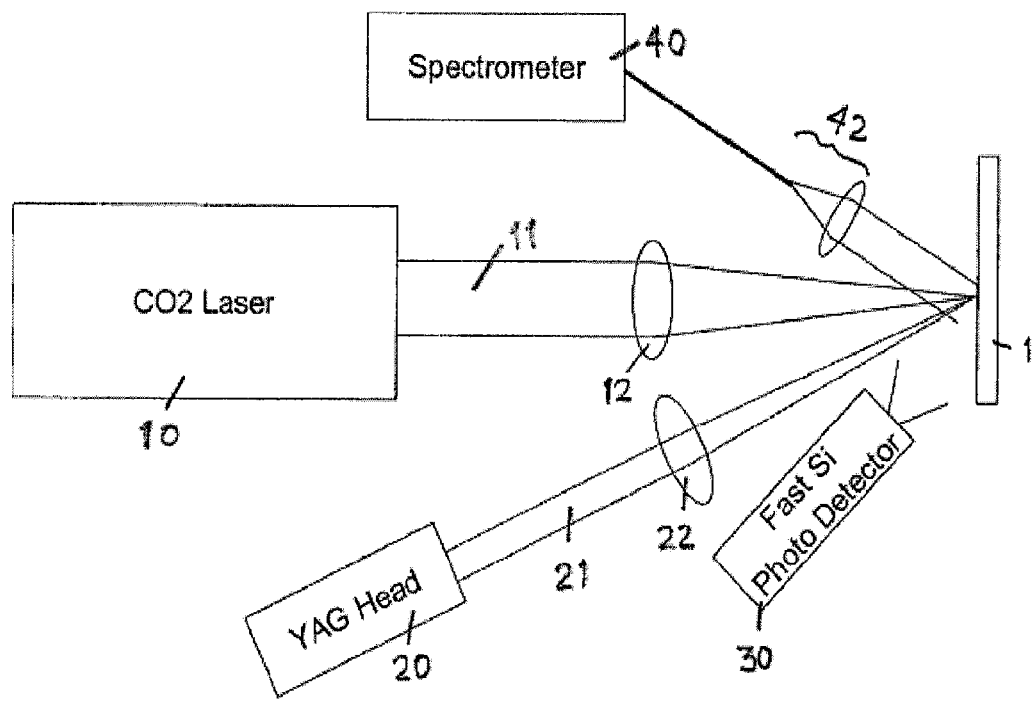
FIG. 4

FIGURE 10
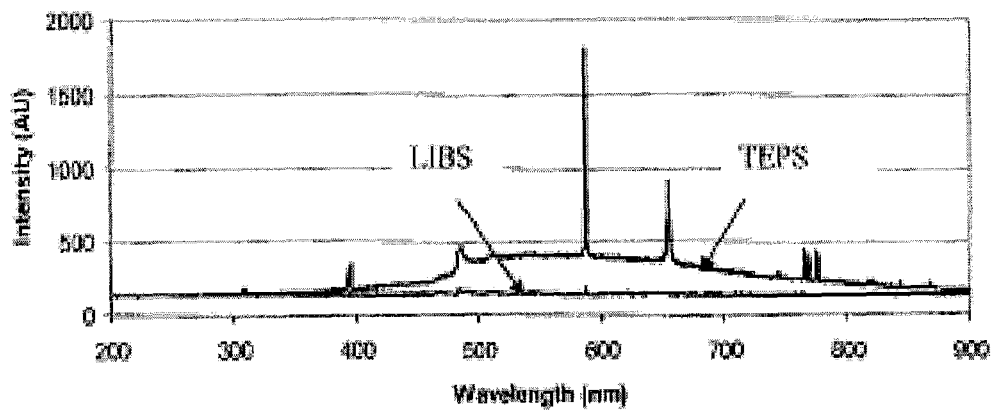
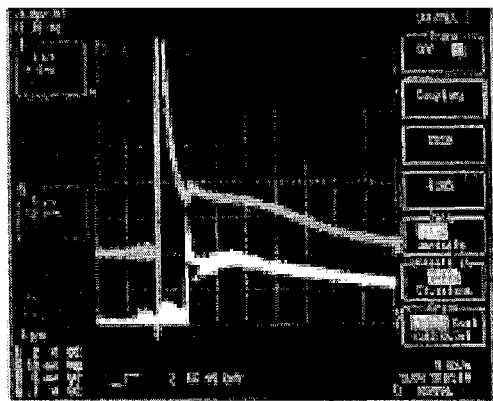
FIGURE 11A
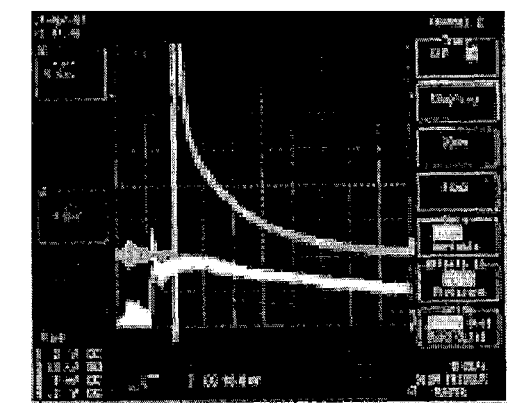
FIGURE 11B
CO2 LASER
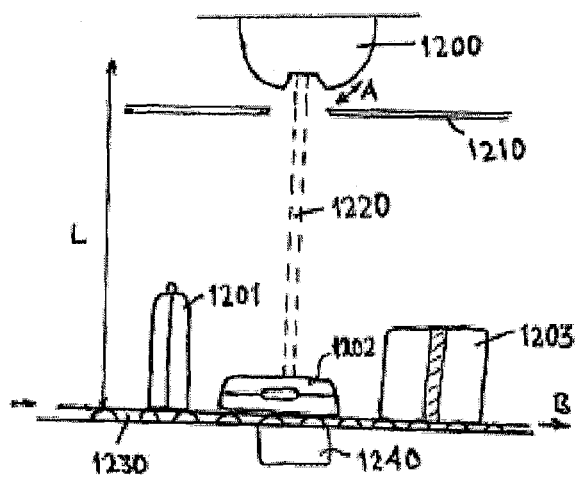
FIG. 12

LASER SPECTROSCOPY SYSTEM

CROSS RELATED APPLICATIONS

This application is a National Stage of PCT/US2008/061809 filed on Apr. 28, 2008 which claims the benefit of U.S. Provisional Application 60/914,658, filed Apr. 27, 2007, which is incorporated by reference herein in its entirety.

GOVERNMENT LICENSE

The U.S. Government may have a paid up license in this invention and the right in limited circumstances to require the patent owner to license others on reasonable terms as provided for by the terms of Contract No. W911QXO7C0044, awarded by the Department of the Army on 2 Mar. 2007.

FIELD OF THE INVENTION

The field is pulsed plasma spectroscopy using a plasma generated at a surface for detecting substances at or near a surface.

BACKGROUND

A carbon dioxide laser is a gas laser, which was invented in 1964 by Kumar Patel of Bell Labs, and is known to be one of the highest power, continuous wave lasers available. A carbon dioxide laser produces a beam of infrared light with a principal wavelength of 9.4 or 10.6 micrometers. In the examples of the summary and detailed description the 10.6 micrometer (10,600 nanometer) wavelength is used. The gas used in commercially available carbon dioxide laser is typically about 10-20% carbon dioxide, 10-20% nitrogen, a few percent of hydrogen or xenon, and a remainder being helium. Special materials are used for the optics and mirrors of a carbon dioxide laser, which operates in the infrared spectrum. Mirrors may be made of coated silicon, molybdenum or gold, while windows and lenses may be made of germanium or zinc selenide. In early versions, lenses and windows were made of crystalline sodium chloride or potassium chloride. On one end of the laser a total reflector is placed and on an opposite end a partially reflective mirror or output coupler may be placed, providing for a continuous infrared laser beam. The percentage of infrared energy reflected may be in range from five to fifteen percent, typically. Edge coupling may be used to reduce optical heating. Power of a carbon dioxide laser may be selected from milliwatts to hundreds of kilowatts in continuous wave setups, but output power may be gigawatts in a q-switched setup. A modulator may be used to externally trigger a q-switched carbon dioxide laser. For this reason, commercially available carbon dioxide lasers are used for industrial cutting and welding applications and for surgical lasers, to a lesser extent. Military uses of carbon dioxide lasers are limited to range finders, laser designators, and laser detection and ranging applications (LADAR). The trend is to replace carbon dioxide lasers with solid state lasers that are more compact, more robust and easier to maintain in a field environment.

Near-infrared and ultraviolet wavelengths may be dangerous for eye safety at high power and short ranges, generally, because there are no visual cues that warn a person that high intensity light is impinging on the retina, as there would be in a visible laser light. Visible laser light may dazzle a person, but it is unlikely to damage the retina, unless high power is used. However, ultraviolet wavelengths may be easily shielded using glass or plastic barriers. One of the concerns for military uses is that the observation of the battlefield using binoculars, scopes or other magnifying devices may collimate and/or focus laser light, which increases ocular damage. The lenses of such devices shield the viewer from some ultraviolet radiation and virtually all of the beam emitted from a carbon dioxide laser. Thus, standards for "eye safe" laser power and wavelength have been established and adopted by the military use and standards setting bodies for which designers of laser emitting systems must be cognizant, such as FDA/CDRH21 CFR 1040 Performance Standard for Light-Emitting Products. "Eye safe" means the power and wavelength of a laser considered "eye safe" by FDA/CDRH21 CFR 1040 and military specifications, depending on the specific application for which a system is intended for use. Thus a laser system for use as a stand-off detector in urban and rural environments must meet eye safe requirements of the military, for military applications such as a detection of hazardous chemical and explosives residue. Infrared and far infrared may damage a cornea, but do not focus on the retina, due to their longer wavelengths. Thus, infrared lasers are considered to be safer than visible light, provided that the power and intensity of the beam are within safe limits. However, infrared wavelengths are difficult to achieve, while maintaining beam output power, using solid state lasers that are preferred in commercial and military applications. Thus, eye safe lasers are considered to have disadvantages that have limited or prevented their use in laser induced plasma spectroscopy.

Nd:YAG lasers are known that emit light in the ultraviolet wavelengths. Nd:YAG lasers may be frequency shifted, have high power outputs, may be pumped using stable, longlasting laser diodes or Diode Pumped Solid State (DPSS) lasers, and are suitable for use in applications that require a hardened, robust laser system. Nd:YAG lasers are the most common lasers used in laser range finding and have virtually replaced carbon dioxide lasers in military and civilian laser range finding. Pulsed Nd:YAG lasers are commonly used for cutting and welding applications for steels and superalloys at a power in the range of 1 to 5 kilowatts, replacing carbon dioxide lasers for all but the highest power applications. In q-switched Nd:YAG lasers, power outputs of 20 megawatts may be obtained. Very compact devices are affordable and are used for applications from golf to the home improvements. The output wavelength of Nd:YAG lasers, without frequency shifting, is 1064 nanometers, but there are also transitions near 940, 1120, 1320 and 1440 nanometers. Frequency shifting and/or addition provides green, blue and yellow visible light output, as well. However, it is important to avoid wavelengths from 400 to 1400 nanometers due to the magnification attributed to the human cornea focusing these wavelengths on the retina, resulting in permanent damage to the retina, especially at high power. For example, FIG. 22 illustrates a relationship between wavelength and a maximum eye safe laser power for a 50 millimeter diameter laser beam (collimated or incident diameter at the cornea).

Er:YAG lasers are known that emit light in the infrared with a wavelength of 2490 nanometers. Er:YAG lasers are often used as surgical lasers, because the energy is readily usable for heating water molecules. The compact size, electronic integration, stability and robustness of these solid states lasers have displaced much of the use of carbon dioxide lasers, which are frequently relegated to applications that require high power beams for cutting and welding, for example.

Frequency doubled Nd:YAG lasers have a wavelength of 532 nanometers (green light), which may be used in certain laser eye surgeries. Frequency doubled and tripled Nd:YAG lasers may be used for specific applications. Frequency shifting may be accomplished using nonlinear optical materials, such as lithium triborate.

A plasma is one of the phases or states of matter. The others are solid, liquid and gas. A plasma is defined as the state of matter in which electrons are dissociated from the nucleus of an element. Thus, a plasma is sometimes referred to as an ionized gas, although the two states of matter are independent from one another. Lightning is known to create a plasma. Even a spark of sufficient intensity is capable of generating a plasma.

Light and other electromagnetic radiation are capable of energizing electrons. For example, radio waves (a type of electromagnetic radiation) are produced by the effect of an alternating currents on electrons in a conductor acting as a transmitting antenna. They are detected by the effect of the radio waves on electrons in a receiving antenna. The effect of various wavelengths of energy on the energizing of electrons in conductors is well known; however, it is less well known how to energize electrons in a plasma.

Pulsed plasma spectroscopy using a pulsed laser to ablate material from a surface is known. However, the laser power required is high, requiring a laser with sufficient energy, focused on the surface at such intensity, that a significant amount of the surface material is ablated. In some applications, it is preferred to leave a surface unmarred by the inducement of a plasma. Also, high power lasers are an eye hazard, which must be avoided in actual practice, unless eye safe frequencies of the emitted laser beam are used. A range of eye safe wavelengths for laser light are known. Retinal damage is the most severe form of eye damage, which must be avoided at all cost in an open field environment. Thus, certain wavelengths that are not capable of causing retinal damage are preferred. In some circumstances, wavelengths in the ultraviolet range are acceptable as eye safe wavelengths, because any damage may be avoided by either limiting the power output of the laser or shielding vision using a clear glass or polymer barrier. One specific hazard is encountered when lasers are used on a battlefield. Anyone observing the battlefield using optical magnification, such as binoculars, is even more susceptible to eye damage from some laser wavelengths. Laser wavelengths in the ultraviolet are attenuated by the lenses in binoculars. Thus, ultraviolet or longer wavelengths are preferred for military applications of laser spectroscopy systems.

Laser-Induced Breakdown Spectroscopy (LIBS) is one example of a plasma spectroscopy. LIBS is also referred to as Laser Spark Spectroscopy (LASS) or Laser-Induced Plasma Spectroscopy (LIPS). The technique was first developed at Los Alamos National Laboratories and involves focusing a laser pulse onto a surface. The energy from the pulse heats, vaporizes, atomizes and then ionizes the material on the surface, resulting in a small, hot plasma. The atoms and ions in the plasma emit light which is then detected and analyzed. Each element has a unique spectral signature, which allows each of the elements in the plasma to be identified. This technique has been applied to the rapid analysis of metals for the purpose of sorting and/or monitoring composition during processing. It has been proposed that a LIBS unit could be fit on a military vehicle or a man portable device for use as a detector for land mines and the like; however, it is believed that no practical device has been tested in the field. One specific shortcoming of known systems is that the laser light is produced using a Nd:YAG laser at high power and at a wavelength that is not eye safe. Frequency shifting of the Nd:YAG laser may be used to shift the output of the laser into the ultraviolet range, but we do not know of any system that has successfully demonstrated a successful test of such a system at a stand off distance of twenty meters or greater. Preferably, any LIBS, LIPS or LASS system would operate at an eye safe wavelength and at a stand off distance of up to 50 meters or greater to reduce the chance of injury during detection of explosives, for example. No known system has demonstrated a fifty meter stand off distance at an eye safe wavelength at least in the ultraviolet range.

The main shortcomings of such systems is the need for a high power laser that increases the power consumption, creates a potential for severe eye damage, and requires impractical sensitivity of the collection optics required for a practical device, including frequent tuning and calibration, for example. In order to achieve a highly focused beam directly on the surface of a target for generating the required plasma with a strong enough signal to detect at any reasonable stand-off distance from the source of the laser, all of the shortcomings of LIBS, LIPS and LASS are present or must be accounted for. Safety of such a laser system is a primary concern, since high power is needed and laser wavelengths that create an eye hazard are typically used for generating the plasma. Lasers are known to cause damage to eyes, and even reflected radiation of high power devices such as required in LIBS may be hazardous to vision.

The Townsend Effect was first described by Sir John Townsend in 1915 in his book *Electricity in Gases* (Oxford University Press, London). In his example, he used a low pressure chamber to contain a gas, X-rays to generate a plasma, and parallel plates to generate an electric field. Townsend realized that there was a mathematical correlation between amplification of the plasma, the gas pressure, and the magnitude of the electric field generated by the parallel plates. It is believed that nobody has previously appreciated that the Townsend Effect may be used to amplify the signal of a plasma created using a laser, such as in LIBS, and no use of the Townsend Effect has been made at a stand off distance from an excitation and amplification source.

SUMMARY

In one example, a field portable plasma spectrometry system has been tested using a LIBS setup at a stand off distance of up to 20 meters. In another example, a stand off distance of 50 meters or greater may be achieved using a carbon dioxide laser to amplify the plasma sparked by the firing of a q-switched solid state laser. In one experimental test of a non-integrated system, using a carbon dioxide laser in close proximity to the target, a laser induced plasma system achieved a stand off distance of 70 meters. A Q-switched laser may be a Nd:YAG, Er:YAG or other laser, such as a solid state laser for compactness, for example, provided that sufficient output power and density is produced for creating a spark plasma. The wavelength of the solid state laser may be frequency shifted to an "eye safe" wavelength at the power used for generating the spark. By using a focal length limited to a certain maximum stand off distance, the beam may be made to be divergent at distances much greater than the maximum stand off distance. Thus, a collimated beam of laser radiation may be avoided that might pose a hazard at distances far from a point of detection on a target.

In one example, a field portable plasma spectrometry system has been tested using a LIBS setup at a stand off distance of up to 20 meters. In another example, a stand off distance of 50 meters or greater may be achieved using a carbon dioxide laser to amplify the plasma sparked by the firing of a q-switched solid state laser. In one experimental test of a non-integrated system, using a carbon dioxide laser in close proximity to the target, a laser induced plasma system achieved a stand off distance of 70 meters. A Q-switched laser may be a Nd:YAG, Er:YAG or other laser, such as a solid state laser for compactness, for example, provided that sufficient output power and density is produced for creating a spark plasma. The wavelength of the solid state laser may be frequency shifted to an "eye safe" wavelength at the power used for generating the spark. By using a focal length limited to a certain maximum stand off distance, the beam may be made to be divergent at distances much greater than the maximum stand off distance. Thus, a collimated beam of laser radiation may be avoided that might pose a hazard at distances far from a point of detection on a target.

In one example, the wavelength and power of both the laser used to spark a plasma and the wavelength and power of the laser used for amplification of the plasma are selected in the eye safe range of wavelengths for the type of beam generated.

In one example, a field portable system is referred to as a Townsend Effect plasma spectroscopy system (TEPS), which solves problems of prior art LIBS devices by applying the Townsend Effect to increase the signal of the emission spectra. One advantage is that the power of the plasma inducing laser may be much less than in a single laser LIBS device, because TEPS amplifies the plasma signal by a much greater gain than is available using single pulse or dual pulse systems. By reducing power requirements inducing a plasma using a laser beam in less eye safe wavelengths, eye damage considerations are further ameliorated using a longer wavelength laser beam for amplification of emissions. Another advantage of TEPS is that testing indicates that the laser amplifying the plasma amplifies the emission spectra peaks without shifting the wavelengths of the peaks. Another advantage is that the output of a carbon dioxide laser is at a wavelength that is more completely shielded by materials, such as a glass lens or glass or plastic protective eyewear, windshields, aircraft canopies, helicopter windows and the like. Yet another advantage is that peaks heretofore not observed in a single laser LIBS of dual pulse system may be observed using amplification of a plasma by a carbon dioxide laser. Yet another advantage of a carbon dioxide laser amplification of a spark plasma is that the enhancement of the signal is independent of the wavelength used to generate a spark plasma.

Yet another advantage is that a carbon dioxide laser has a wavelength capable of heating a surface. In one example, a TEPS system using a carbon dioxide laser may be used to form a hole or melt a portion of the surface of a target, using the beam from the carbon dioxide laser to detect trace elements otherwise shielded by a surface coating or film, for example. Standard LIBS systems teach away from any substantial ablation of an underlying surface, preferring pulsed beams with wavelengths in the ultraviolet that cause substantially no ablation of the substrate surface. The lack of surface ablation of a surface of a target substrate is considered an advantage by the LIBS industry. However, the TEPS system may be operated using the same carbon dioxide laser in a mode for surface ablation or substantially no surface ablation. Surprisingly, the option to drill through a surface is a significant advantage for detection of certain explosives or hazardous chemicals.

Still another advantage is that stand off detection at distances greater than 20 meters, more preferably greater than 50 meters, are achievable for both laser induced plasma spectroscopy and for RAMAN spectroscopy and stimulated RAMAN spectroscopy, using the same instrument and lasers used for laser induced plasma spectroscopy. Laser induced plasma spectroscopy is capable of detecting trace elements and ratios of elements due to the emission signature from a cooling plasma, while RAMAN spectroscopy is cable of detecting molecular bonding information about such trace elements. Thus, a dual TEPS/RAMAN system provides information not only about the elements and ratios of elements present, but also about the molecular bonds present in molecules formed by the elements detected by the TEPS device. This is a substantial advance over LIBS-only devices. One of the disadvantages of combining RAMAN and conventional LIBS is the very limited range of conventional LIBS. By increasing the stand off distance, TEPS systems are capable of matching stand off distances of RAMAN spectroscopy systems. In a dual TEPS/RAMAN system, system components are used to perform both spectroscopic analysis, conserving space and reducing costs compared to separate systems.

In one example, a single laser, operating at an eye safe wavelength and power within the ultraviolet range, is used to detect both laser induced plasma spectroscopy and RAMAN spectroscopy. One or more spectroscopes are coupled to the optics of a telescope to detect emissions from either electrons relaxing from the plasma or the chemical bonds in RAMAN spectroscopy, saving parts and increasing compactness of a dual LIBS/RAMAN eye-safe spectroscopy system.

In another example, A TEPS system is integrated using a second laser but no additional telescope or spectrometer/spectroscope(s). In this example, a common beam director may be used to direct an infrared beam and an ultraviolet beam to a surface of a target. In this system, there are fewer moving parts, improved compactness, improved seal, absence of parallax using a co-axial boresight, and additional advantages. Indeed, the advantages of this integrated system reap the benefits of a greater amplification of the emissions detected while avoiding disadvantages of using a carbon dioxide laser in addition to a solid state laser. A small instrumentation package may be added to the integrated TEPS system for conducting tests and analysis of the integrated TEPS system. The instrumentation package may be mounted on a table, a mobile cart, a cart adjoined to the TEPS system, or on a bracket attached to the side of the TEPS system. The bracket may include a cover to protect the instrumentation package, which may include communications, additional spectroscopic techniques, such as RAMAN and others.

In one example, a TEPS system is capable of amplifying a peak signal detected by a spectrometer by more than 100 times using a carbon dioxide laser with an energy of less than 0.07 Joules per square millimeter ($J/mm^2$) as a source of amplification of a plasma induced by a YAG laser. Another advantage is that the amplification of the plasma using a carbon dioxide laser creates a unique amplification of some emission peaks to a degree that is greater than the amplification of other peaks. In one example, this is used to distinguish the ionized elements in the plasma. In tests using a similar arrangement and detector with a Nd:YAG laser as the amplification source, instead of a carbon dioxide laser as the amplification source, five key peak emission lines were amplified at less than half of the intensity as for the carbon dioxide laser. This is a very surprising and unexpected result. The rest of the industry is using solid state and Nd:YAG lasers for LIBS and other plasma spectrometry applications, and carbon dioxide lasers are relegated to some high power laser cutting or welding applications in the manufacturing industry. Carbon dioxide lasers of the appropriate size and power requirements are not generally available commercially for this reason. In addition, other LIBS providers are drawn to the compact size of the solid state lasers and optics used in designs based on lasers, such as the Nd:YAG laser. However, each of the five emission lines observed using only a YAG laser were amplified by a carbon dioxide laser by at least a factor of twenty times at an energy of less than 0.07 J/mm². Testing has shown an amplification of twenty-five to three hundred times for various peaks of intensity versus wavelength. Thus, the amplification by a carbon dioxide laser was a significant improvement over any known LIBS system.

Yet another advantage of the use of a carbon dioxide laser is an improved range of detection. A carbon dioxide laser has been used for amplification of a spark plasma at a distance greater than 30 meters and up to 70 meters from the laser induced plasma spectroscopy system. A carbon dioxide laser may be used for amplification of a plasma with a gain of 25 times to 300 times that of the plasma without amplification, which is much greater than the reported gains for a dual pulse Nd:YAG laser, which have been reported at about 7 times up to a maximum of about 40 times, but no testing of dual pulse Nd:YAG setups, utilizing setups similar to the carbon dioxide laser, were able to produce gains greater than about 9 times the signal from the initial plasma. Preferably, a stand off distance is selected to be greater than the stand-off distance for an explosive device, which may be 50 to 100 meters for an armored or shielded combat vehicle searching for improvised explosive devices of unknown size and lethality or less for unexploded munitions or land mines of a known make and model, for example. In yet another example, the stand-off distance provided by a TEPS system may be greater than 100 meters. Some prior art devices were limited to detecting samples having at least 8% concentrations of the compound to be detected, but TEPS is capable of measuring very dilute amounts of trace compounds on surfaces for multiple energetic compounds, simultaneously.

Another advantage is a plasma spectroscopy system using laser beams having wavelengths that are eye safe at the energies required for stand-off detection of high explosives or hazardous substances. This has the benefit of increasing ocular safety and the ability to make detections with the device in closer proximity to humans. Yet another advantage is a reduced false negative rate. Yet another advantage is a reduced false positive rate.

BRIEF DESCRIPTION OF THE FIGURES

The drawings illustrate some examples and results that are describe in the detailed description.

FIG. 3A illustrates a perspective view of another example of a stand-off laser-induced plasma spectroscopy system, including a second laser integrated in a system using a common beam director.

FIG. 3B illustrates a cut-away view of the example in FIG. 3A.

FIG. 3C illustrates an example of beam pathways and optics for integrating two laser beams of differing wavelengths in the example of FIG. 3B.

FIG. 3D illustrates an example of pathways for emissions from a target that are collected by one or more spectroscopes and a camera.

FIG. 3E illustrates a detailed view of an example of an optical element permitting emissions to reach one or more spectroscopes and a laser beam to be focused on a target.

FIG. 3F illustrates an optional instrumentation package added to the system of FIG. 3A using a bracket.

FIG. 4 illustrates, schematically, a block diagram of an experimental TEPS laser spectroscopy system.

FIG. 10 compares the measured intensity signal for one example of a TEPS measurement and a LIBS measurement.

FIGS. 11A and 11B illustrate an oscilloscope showing a time delay of the pulsed laser beams in a TEPS system.

FIG. 12 illustrates an example of an application for a TEPS/RAMAN system.

DETAILED DESCRIPTION

Figure 1A:
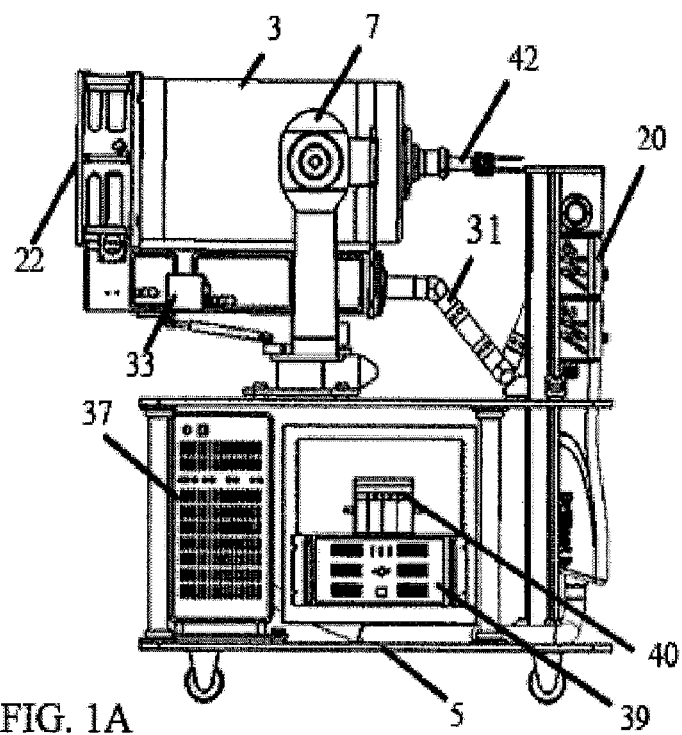
FIG. 1A illustrates a side plan view of an example of a stand-off laser-induced plasma spectroscopy system.
Figure 1B:
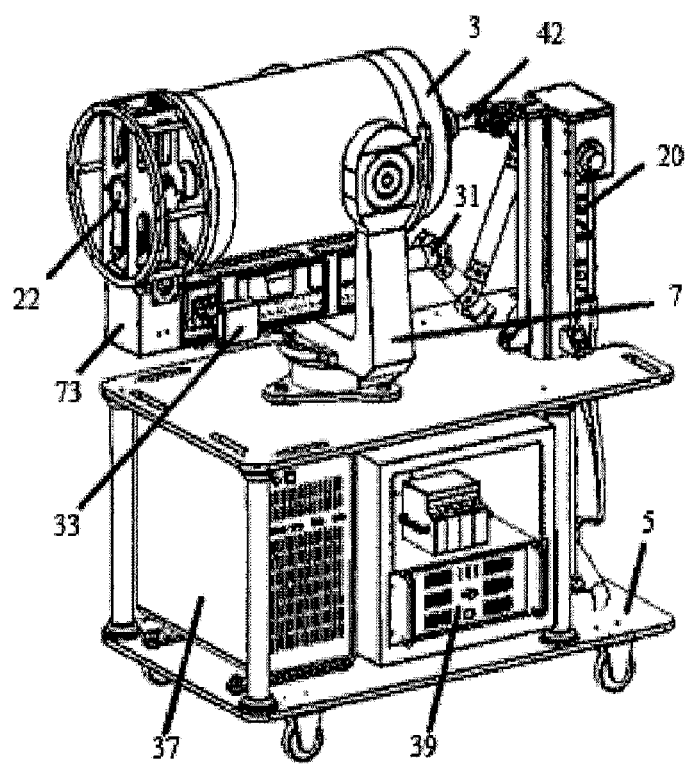
FIG. 1B illustrates the same example in a perspective view.

FIGS. 1A and 1B illustrate a solid state laser system for use in stand off detection at a distance up to 20 meters. For example, one or more Nd:YAG lasers may be integrated in a laser system 20. For example, each Nd:YAG laser has an eye-safe, frequency-shifted beam with a wavelength of 266 nanometers. Devices using a Nd:YAG laser frequency shifted to 355 nanometers have reportedly failed to achieve stand off detection distances of 20 meters for explosives residues in testing by others. In this example, a telescope 3 for collecting emissions from laser-induced plasma spectrometry is disposed on a mount 7 directionally controlled by a telescope mount and having beam transport controlled by an articulated arm 31. A laser range finder 33 provides a distance to a target, allowing the optical system to focus a first beam generated by a first laser at a desired focal length, using a beam expander or focusing lens 22. The entire system is mounted on a mobility platform 5, such as a cart, robotic platform, vehicle, or airframe. The mobility platform 5 integrates a power supply 37, a system controller 39, and one or more spectroscopes 40 for detecting the frequency of emissions from an induced plasma. The emission are collected and focused by the telescope 3 and are directed to the spectroscopes 40 using optics and/or optical fiber, such as a collimator and optical fiber system 42. In addition, a second beam of a second Nd:YAG laser may be pulsed after a time delay to enhance the detected emissions, and the second beam may be an eye safe, frequency-shifted wavelength, such as 266 nanometers.

Figure 1C:
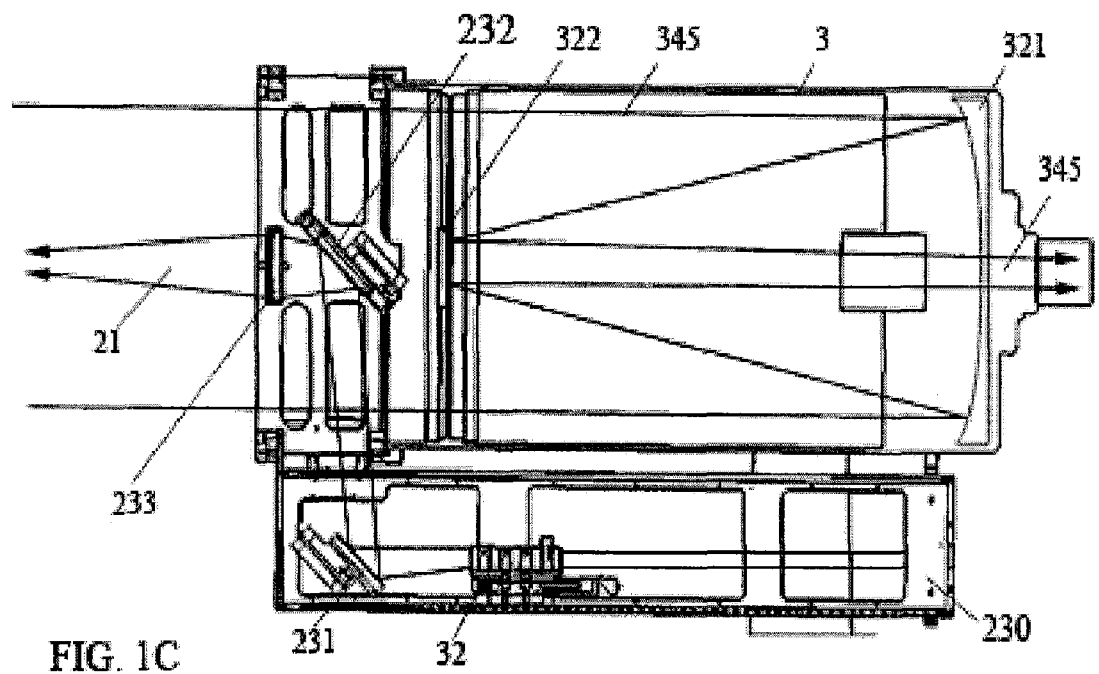
FIG. 1C illustrates a detail, cut-away internal view of a telescope for transmitting a focused laser beam and receiving emissions from a target.

FIG. 1C illustrates one example of an optical system for use in the telescope 3 of the example of FIGS. 1A and 1B. An output beam 21 is focused by a optical lens 233. The laser beam 21 is input to an optical alignment system 20. The optical alignment system may have a diverging lens 32 for adjusting the focal length of the beam. The divergent beam may be directed by a first reflector 231 to a second reflector 232, which may be optically aligned with the optics of the telescope 3. The output beam 21 may be optically aligned using this alignment system or other alignment systems. One advantage of the alignment system is the capability of adjusting the focal length of the beam to correspond with a surface of a target 1, for example. Laser-induced emissions are collected by the telescope 3, which is aligned with the target 1, for example. The alignment mirror 232 may block some of the emissions; however, an annular collection region may be used to capture an adequate sampling of the emissions using an objective 321 and a secondary mirror 322, such as in a cassegrain reflector telescope. The objective 322 may be a parabolic minor, for example, which directs the emissions entering the telescope 3 onto a secondary mirror 322. The advantage of a cassegrain reflector arrangement is its well known ability to shorten the length of a telescope's optics, which is preferable for operation of a mobile device. The emissions 345 may be collimated and captured by a fiber optics (not shown). Then, fiber optics may be used to deliver the captured emissions 345 to one or more spectroscopes 40, 111 as shown and described in the various examples in FIGS. 1A-3E and 13, for example.

In one example, use of a Nd:YAG laser at a frequency-shifted wavelength of 266 nanometers was capable of detecting the signature of an explosive at a distance of up to 20 meters. Due to the lack of success by others at discriminating emissions of an explosive using a frequency-shifted laser, this success is both surprising and unexpected for a Nd:YAG laser frequency shifted to a wavelength of 266 nanometers. A system configured according to FIG. 1 is capable of detecting trace elements on a surface at 20 meters, by generating a spark plasma using a Q-switched Nd:YAG laser capable of emitting a high power, frequency shifted beam at a wavelength of 255 nanometers.

For example, an optical system focused a beam, having an output power in a range from 20 milliJoules to 200 milliJoules to a spot density from 20 milliJoules per square millimeter to 20,000 milliJoules per square millimeter. The spot size may have a diameter in a range from 0.01 millimeters to 1 millimeters. The initial pulse has a pulse width at half maximum in a range from 1 nanosecond to 100 nanoseconds.

A plasma enhancing laser may use a second Nd:YAG laser at the same frequency-shifted wavelength and having similar characteristics, for example. Alternatively, the plasma enhancing laser may have a different wavelength and pulse width.

In Table 1, the output power, spot sizes and pulse widths at half maximum, peak-to-peak delay, and gain (ratio of intensity of selected peaks to intensity without the use of the amplifying second laser) are shown for a device configured as in FIG. 1 with two Nd:YAG lasers frequency shifted to 266 nanometers.

TABLE 1

Experimental Data

| Output Power (mJ) | | Spot Diameter (mm) | | Pulse Width (nanosec.) | | delay (µsec.) | gain |
|---|---|---|---|---|---|---|---|
| laser 1 | laser 2 | laser 1 | laser 2 | laser 1 | laser 2 | | |
| 40 | 100 | 0.1 | 1 | 5 | 5 | 2 | 6 |
| 40 | 100 | 0.1 | 1 | 5 | 5 | 4 | 12 |
| 40 | 100 | 0.1 | 1 | 5 | 5 | 10 | 10 |
| 40 | 100 | 0.1 | 1 | 5 | 5 | 16 | 4 |
| 100 | 40 | 1 | 0.1 | 5 | 5 | 2 | 6 |
| 100 | 40 | 1 | 0.1 | 5 | 5 | 4 | 12 |
| 100 | 40 | 1 | 0.1 | 5 | 5 | 10 | 10 |
| 100 | 40 | 1 | 0.1 | 5 | 5 | 16 | 4 |

Figure 2:
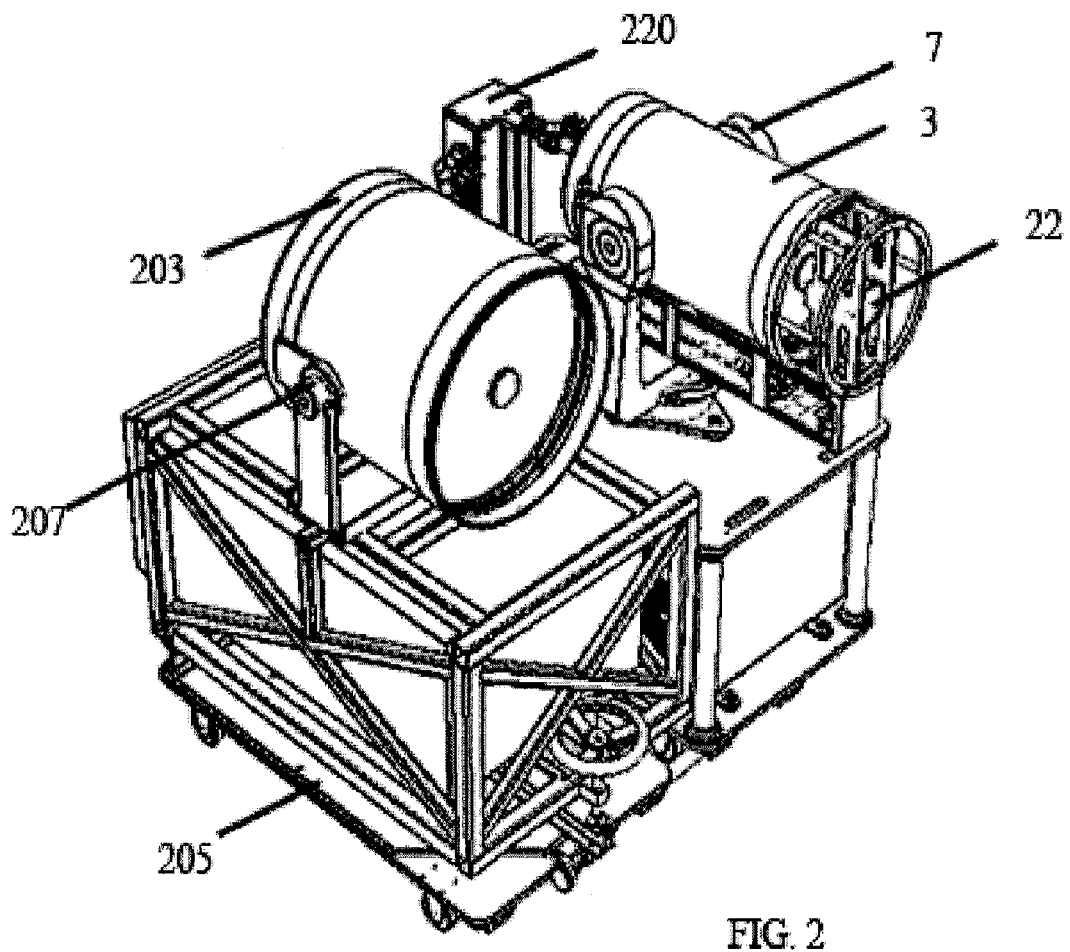
FIG. 2 illustrates a perspective view of another example of a stand-off laser-induced plasma spectroscopy system, including a second laser and focusing optics mounted on a mobility platform.

In FIG. 2, the first laser housing 220 comprises a first laser for use in inducing a spark plasma, while, the second laser 210 has a beam with a substantially longer wavelength than that of the first laser and is used to enhance the spark plasma or as a source of excitation for RAMAN spectroscopy. The optical system for the first laser may be arranged as shown in FIGS. 1A-1E, for example. Alternatively, the optical system for the first laser may be aligned as shown in the example of FIG. 3C or otherwise, which is described in relation to the example shown in FIGS. 3A-3E. The lasers and optics may be mounted on a mobility platform 205. Mounts 7, 207 may be used to mount optics 3, 203 for the first laser, housed in the laser housing 220, and the second laser 210, respectively. In one example the first laser is a Nd:YAG laser having a frequency doubled beam having an eye safe wavelength, power and divergence, such as the Nd:YAG laser having a wavelength of 266 nm used for inducing the spark plasma in one example for the system of FIG. 1A. The second laser 210 may be a carbon dioxide laser or another laser emitting a beam at a wavelength in the infrared, such as 10,600 nanometers, for example. Gimble mounts may be used for the mounts 7, 207, for example. A parabolic mirror may be used as a beam diverger and for focusing of one or both of the two lasers and/or the emissions from the induced and amplified plasma. In one example, the systems is a TEPS, and is capable of stand-off distances of greater than 20 meters. In another example, the system is capable of stand-off distances greater than 50 meters. A gain induced by the second laser 210 may be greater than 20 times the unamplified plasma emissions, more preferably, greater than 50 times the unamplified plasma emissions for a plurality of peaks associated with elements to be detected. In one example, a system has a gain for peaks of twenty-five times to three hundred times that of unamplified laser induced plasma emissions.

Whichever alignment system is selected, the first laser may be focused on a target, and the second laser 210 may be used to amplify the emissions from the plasma induced by the first laser when it is focused on a surface of the target. For example, optics may be capable of focusing the laser beam generated by the first laser, having a power of 100 mJ, to a spot diameter of 1 millimeters. The first laser may be Q-switched electronically using a pockel cell, for example, which may generate a pulse width at half maximum in a range from 2 to 20 nanoseconds. The second laser is switched to provide a power output in a range from 100 to 10,000 milliJoules with a spot diameter in a range from 1 to 10 millimeters and a pulse width at half maximum from 10 nanoseconds to 1 microsecond, for example. The peak-to-peak delay between the pulse of the first laser and the second laser may be from 0 to 5 microseconds, preferably from 0.25 to 3 microseconds, more preferably, less than 1 microsecond. In one example, a delay of 0.5 microseconds is selected for improving gain and differentiation of gain between certain peaks.

FIGS. 3A and 3B illustrate a laser spectrometry system having a first laser 2 and a second laser 520, emitting a different wavelength of light from the first laser 2, integrated into a compact optics system, such that the beams of each of these two lasers are aligned by a common beam director assembly 572 capable of aiming the two beams on a target using a mount 507, such as an automated Gimble head mount. A single output port 522 provides for unobstructed laser beams of the first laser 2 and the second laser 520 toward a target. In one example, as shown in FIGS. 3C and 3D, optical pathways 545, 521, 11 are shown in a cut-away view of a telescope 503 and alignment optical system, which is capable of aligning the beams of the first laser 2, the second laser 520 and the amplified emissions 545 of an induced spark plasma. The telescope 3 is integrated in a protective housing 501 with a power supply 537, a controller 539, which may include a computer and delay generators, one or more spectroscopes 511, a camera 575 coupled to the spectroscopes by a beam splitter 581, such as a 90/10 beam splitter for directing about 10% of emissions to the camera, a rangefinder 33, and the two lasers 2, 520 and the optics necessary to align the lasers with the axis of the telescope 3. In the example of FIG. 3C, the first laser 2 is aligned along the axis of the telescope 3 using a reflector 572, which is capable of transmitting the beam of the laser 2 while not blocking the emissions received by the telescope 503 from the spark plasma.

For example, FIG. 3E illustrates an example of a reflector 572 that allows one of the beams to be reflected, such as from the center 831 or the annular periphery 832, while the other beam is transmitted through the other portion of the reflector 572. One example is a Pierce reflector, which allows light to pass through a center region 831, while reflecting light from the annular region 832. In this example, the beam of the first laser may be annularized, for example, to emit from the telescope through divergent or focusing optics 522 to be focused on a surface of a target. Although the beam paths shown in FIG. 3C are shown to be emitted straight from the telescope, the optical system may include diverging and focusing optics in the telescope 3 and/or in the beam director 572 using known optical elements, such as mirrors/reflectors, lenses, diffraction gratings and the like to focus the annular beam 521 on a surface of a target. In the example of FIG. 3C, a laser 520, such as a carbon dioxide laser, has a beam 11 aligned by alignment optics along the axis of the telescope 3 and aimed at or near the surface of a target by the optics and beam director 572. The beam divergergence and focusing optics may be similar to those illustrated in the example of FIG. 1C, for example. For example, a focused beam of 10,600 nanometer wavelength of a carbon dioxide laser may be directed and focused on a spark plasma after a delay set by the controller 539. In one example, the delay is less than 3 microseconds, providing an application of the emissions of more than 50 times for a plurality of peaks corresponding to elements to be detected by the system compared to emissions from the spark plasma without amplification of the emissions by the carbon dioxide laser. The delay time may be less than 1 microsecond in another example with a peak gain of more than 100 times that of the unamplified emissions of a spark plasma generated by a single Nd:YAG laser having an eye safe beam at a wavelength of 266 nanometers.

The beam director 572 may use any optics capable of directing both a beam of a first laser 2, having a frequency adjusted wavelength of 266 nanometers for example, and a beam of a second laser 520, having a wavelength of 10,600 nanometers for example. To the extent that one beam is directed along the central axis of the telescope 3 and the other beam is directed along an annular region of the telescope 3, it is a matter of selecting coatings and materials along each of the beam pathways that are capable of directing each of the beams to a specified target point. In one example, the laser range finder 33 is used to adjust the focal optics to focus one or both of the lasers on or near a surface of a target.

In one example the spectroscope 575, shown schematically in FIGS. 3C and 3D include a plurality of spectroscopes coupled by fiber optics to the laser induced emissions 545. In this example, the system may be used to provide an amplified, laser-induced breakdown spectroscopy data, using both a YAG laser and a carbon dioxide laser for example, and RAMAN spectroscopy data using only one of the lasers but the same instrument and optics. In this example, the "multi-spectral" data may be combined to determine both the presence of certain elements using TEPS and the presence of certain chemical bonds using RAMAN. The synergy of the combined system, without the added expense, maintenance and alignment difficulties of using two separate devices, provides for a unique confirmation of the presence of certain signature chemicals, which may be used to identify a threat, such as the presence of explosives residues on surface or the presence of another hazardous or toxic substance or pollutant.

In one example, the combination of TEPS and RAMAN is compared against certain emissions signatures in a look up table (LUT) to quickly identify the presence or absence of specific threats. For example, the LUT may be modified from time to time based on mission parameters to detect specific threats that are known to exist in a theatre of operations. In one example, the LUT is securely stored in storage medium. In another example, the LUT may be securely downloaded from a trusted source, such as by downloading over a secure network. In yet another example, only a portion of the LUT may be downloadable and the remainder of the LUT may be securely stored in a storage medium coupled to the controller 539 or within the controller 539.

In another example, advanced chemometric algorithms, such as available for commercially available software such as MATLAB™[1], are solved by numerical algorithms. For example, a partial e-squares analysis or a transmission fitting method may be used, among others. In one example, the signal from one or more spectroscopes is processed using an advanced chemometric algorithm. The result is output to a user as a go/no go display, such as a green light for safe and a red light for danger. In one example, the danger is further delineated as to type, such as explosive or chemical hazard. In yet another example, the red light blinks while the green light remains steady. The red light may remain blinking until cleared, for example. In yet another example, a system generates an audible alert. The operator interface may be a computer, which may provide the operator with an input device, such as a joy stick, track ball or mouse for controlling aiming of the lasers on a target. In one example, the camera uses the telescope 3 optics to magnify the view of the operator on a screen or projection, such as a monitor of a terminal, a laptop screen, a screen of a handheld device or heads up display. In one example, a stand off distance of 70 meters was achieved in a test system having all of the optics, except for a carbon dioxide laser of a TEPS system, at a distance of 70 meters. In this test a carbon dioxide laser was located at close range to the target in order to test the physics and optics of the system. As shown in FIGS. 3A-3B, a carbon dioxide laser may be co-located with the other laser and optical components, or the carbon dioxide laser may be separate, as illustrated in FIG. 2.

FIG. 4 shows a schematic illustration of a Townsend Effect Plasma Spectroscopy (TEPS) system for use in detecting emission spectra from surfaces. The test sample 1 was ceramic in one test, but the TEPS system may be used for detecting emission spectra of even trace contaminants on a surface and for surface analysis of many other materials. Indeed, a TEPS system may be used with a laser to ablate a portion of the surface or may be used to avoid, as much as possible, ablation of a surface to measure primarily contaminants on a surface. Alternatively, in conjunction with a high power laser, a TEPS system may be used to analyze below a surface layer by ablating away a surface. Vapor can be analyzed by focusing the plasma formation within the vapor such that the intensity of the beam and the energy of the beam generate a plasma. Without being limiting in any way, one example of TEPS or a related phenomenon is referred to as "reverse Brehmstralung."

It is believed that the wavelengths of the various emission lines are the same as for LIBS or laser ablation—inductively coupled plasma, which is a standard laboratory analytical technique, except for the addition of some lines not previously visible in ordinary LIBS. The intensity of the various emission lines is unique in TEPS, which is useful for detecting specific signatures. With the addition of RAMAN spectroscopy, using the same instrument, a more complete characteristic signature may be compiled for residual substances to be detected by a TEPS/RAMAN system.

In one example, a carbon dioxide ($CO2$ or $CO_2$) laser 10 may be used in FIG. 4 to emit a beam 11 that is focused (or collimated) by optical elements 12 on or adjacent to the surface of an object to be analyzed. A Nd:YAG laser 20 may be selected to emit a second beam 21 that is focused (or collimated) by optical elements 22 at about the same location on the surface of an object to be analyzed. A fast, silicon photo detector 30 may be used to trigger a spectroscope 40, which measures the emitted radiation during cooling of the plasma. For example, the spectroscope 40 may detect emitted radiation in a range from 200 to 1000 nanometers (nm) in wavelength.

Figure 5:
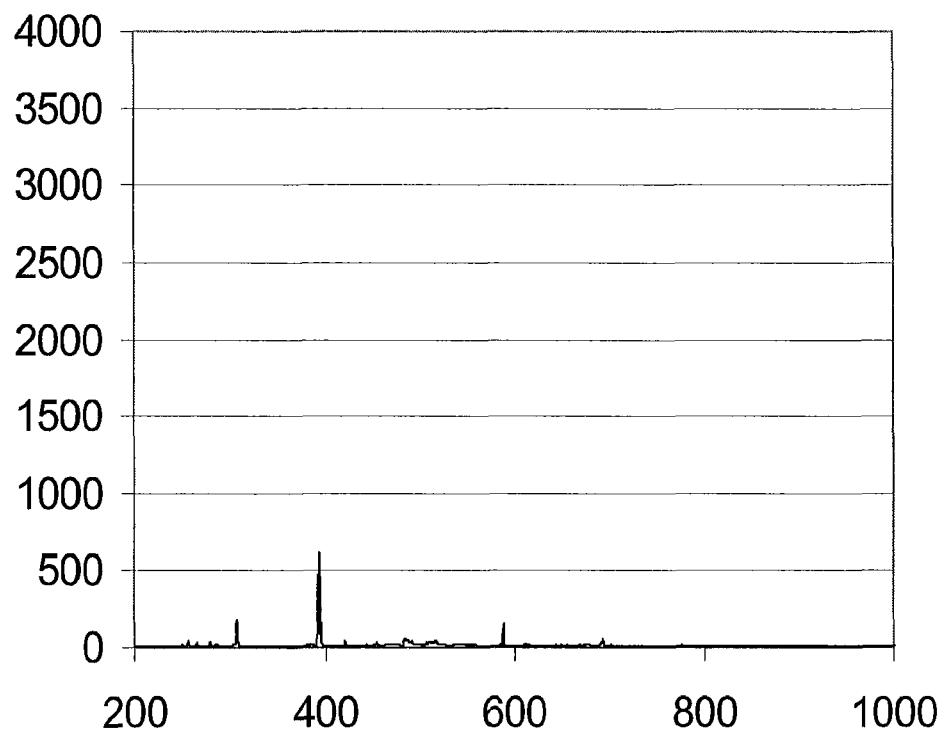
FIGS. 5 and 6 show graphs of intensity in counts versus wavelength in nanometers using (FIG. 5) a single YAG laser generating a spark plasma, and (FIG. 6) a YAG laser in combination with a carbon dioxide laser inducing amplification of the plasma at the longer wavelength of the carbon dioxide laser.

FIG. 5 shows an image of a prototype system used in testing of TEPS on a laboratory bench. In this example, the emitted radiation is transmitted to the spectroscope by a optical fiber and collimator, and in this example, the spectroscope may be located in a unit not aligned with the laser beams.

Figure 6:
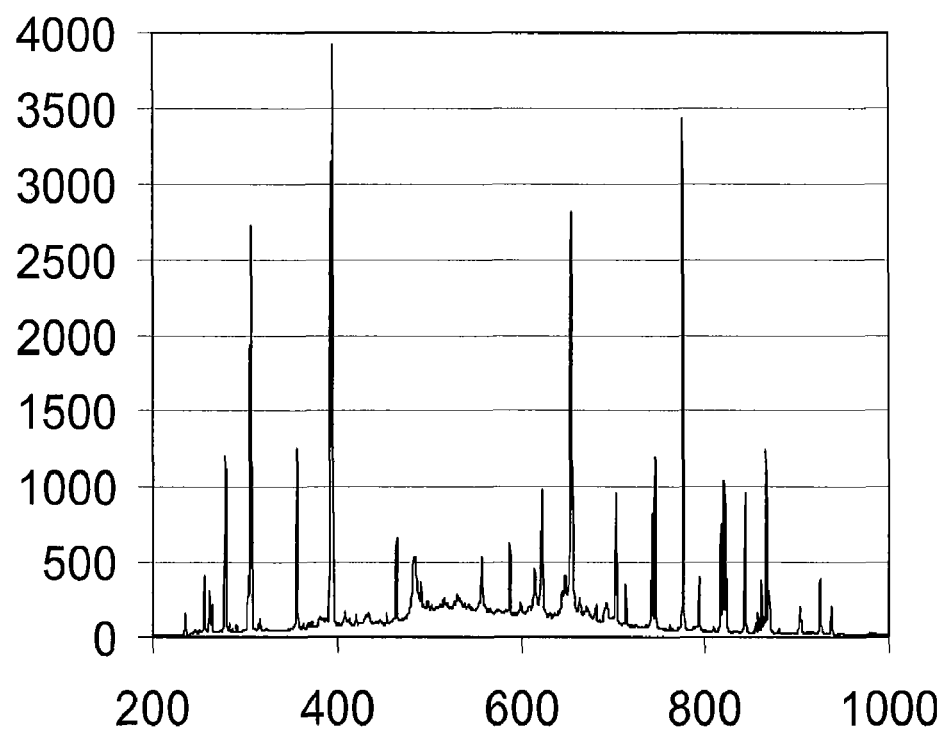

The wavelength of the CO2 laser in one example is 10.6 microns. The beam spot diameter of the CO2 laser may be about 7 mm, for example. In FIGS. 5 and 6, a comparison of the Intensity versus wavelength of detected radiation is displayed that shows that the CO2 laser amplifies the emission spectra detected by the spectroscope. In this example, a Nd:YAG laser was fired at a ceramic target. After a delay of 6 microseconds (µs), the CO2 laser was fired, yielding both an amplification of the previously identified emission peaks and previously unidentified emission spectra that were not apparent.

Figure 7A:
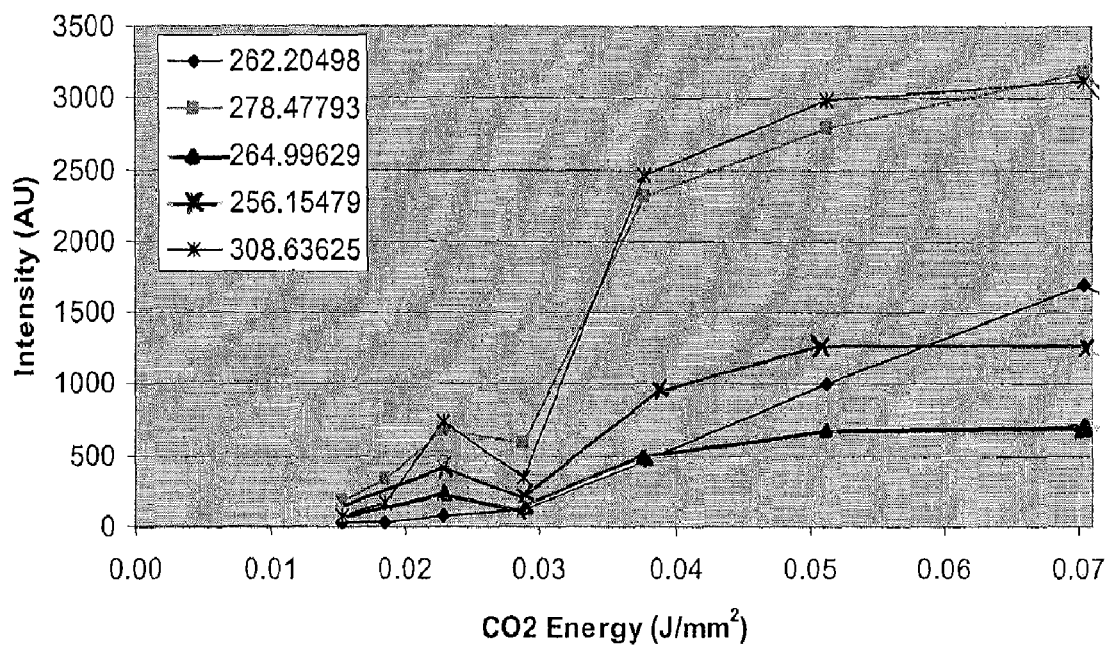
FIGS. 7A and 7B illustrate the effect of varying the energy of the carbon dioxide laser shown in FIGS. 5—on (7A) intensity of the emission spectra for various peak emission lines and (7B) the ratio of the intensity of the same lines with and without Townsend Effect amplification of the plasma by the CO2 laser.
Figure 7B:
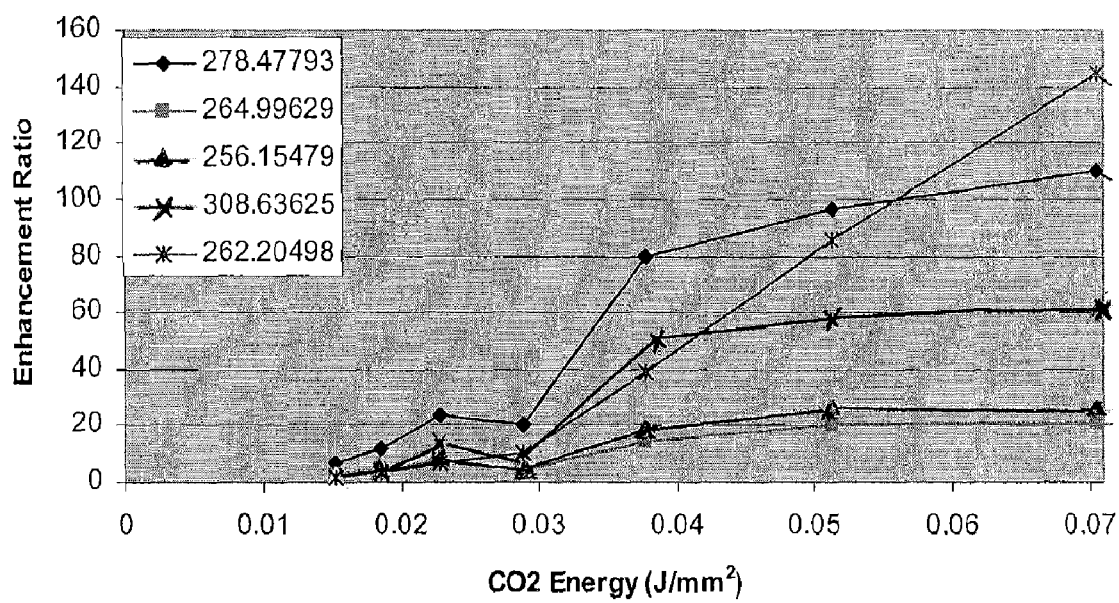

FIG. 7A shows a few of the emission lines using the CO2 laser versus the energy of the CO2 laser used to produce the Townsend Effect for the same TEPS system as shown in FIGS. 5 and 6. A preferred range of CO2 energy at the surface of a target is from about 0.034 $J/mm^2$ to about 0.07 $J/mm^2$ or a range that provides an amplification of the emission spectra of at least 10 times, for example.

The wavelength of the YAG laser is 1060 nanometers, for example, but in other examples the wavelength of the YAG laser is varied and the gain and wavelength of the output peaks is substantially independent from the wavelength of the YAG laser. Thus, TEPS may use any of the available Nd:YAG, Er:YAG or other solid state laser output wavelengths for generating a spark plasma. This is a surprising and unexpected result and an advantage for use of a carbon dioxide laser for amplification of the plasma. The intensity of the YAG laser at the surface of the material to be tested may be in a range from 0.1 $J/mm^2$ and greater, for example. In FIGS. 5, 6, 7A and 7B the intensity of the YAG laser is 0.25 $J/mm^2$ at the surface of the test specimen.

Figure 8:
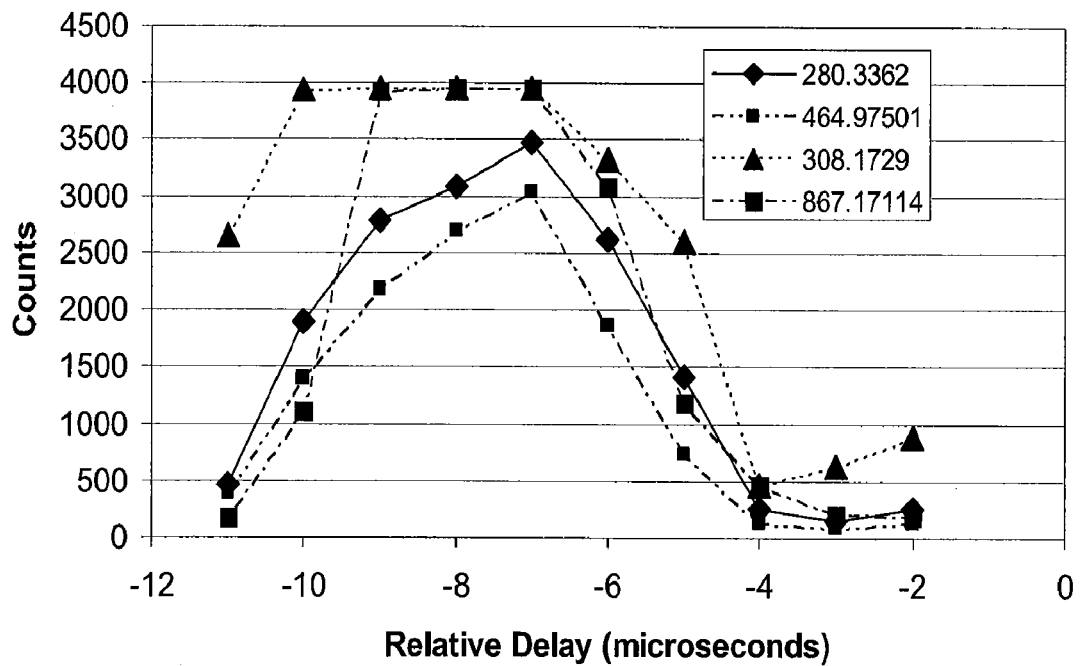
FIG. 8 illustrates the effect of varying the time delay between a pulse of a YAG laser generating a plasma spark and a pulse of the CO2 laser used to amplify the plasma.

In one example, the CO2 laser is fired at the same time or within a few microseconds of a YAG laser, which induces a spark plasma, providing a plasma for the CO2 laser to amplify. As shown in FIG. 8, the amplification is dependent on the time delay. Preferably the time delay is between about 4 and 11 microseconds, more preferably 5 and 10 microseconds, even more preferably between about 6 and 8 microseconds. The amplification of some emission lines is improved by an additional 20% or so for a time delay of 7 microseconds compared to a time delay of 6 microseconds, for example. In this example, the CO2 laser uses a pulsed laser output, such as a Lumonics Impact, Model 950T SSM. For example, in the test, a pulse length was selected to have a gain switched spike having a 100 to 200 ns full width at half maximum and a nitrogen fed tail of 0.5 to 2 microseconds at full width half maximum. In one example, 4000 counts was the maximum of the test instrument and data clipping occurred above 4000 counts. In one example, a low power energy source may be used to power the TEPS system by pulsing the CO2 and YAG lasers, without sacrificing the sensitivity of the measurement and analysis of the TEPS system.

Figure 9:
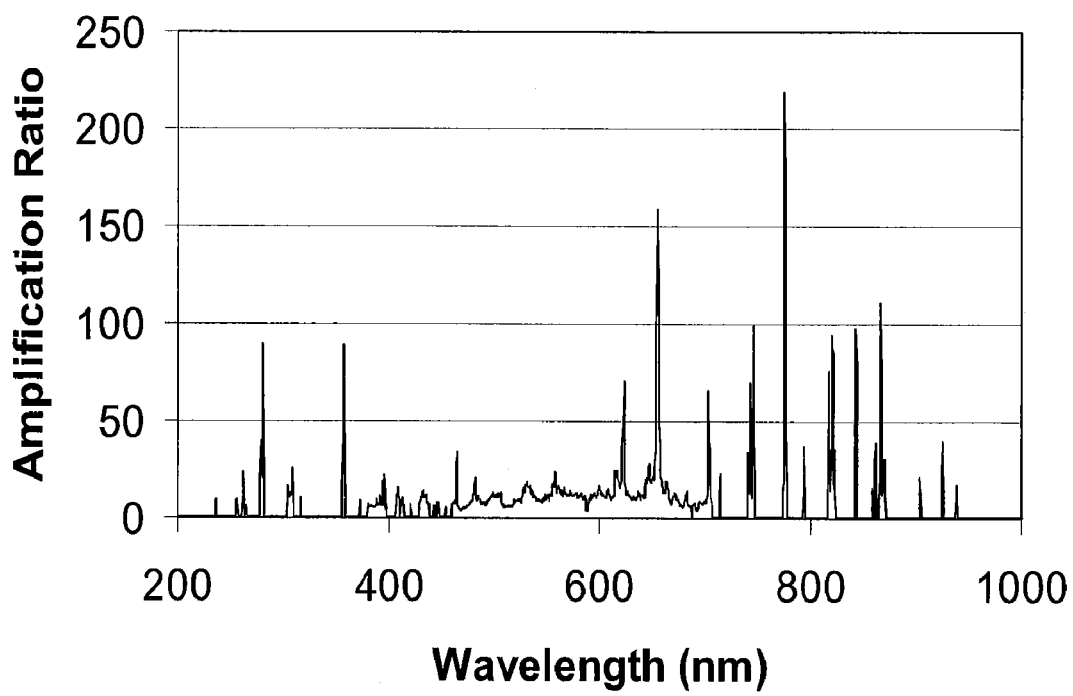
FIG. 9 shows a graph of the gain (ratio of TEPS enhanced signal to LIBS unenhanced signal) for one of the experimental measurements using the system illustrated in FIGS. 4 and 5.

FIG. 9 shows the amplification ratio of the intensity using a carbon dioxide laser for amplification of a spark plasma generated using a Nd:YAG laser source compared to the intensity without amplification of the plasma spark. An amplification of 100 times is unknown in the industry. Typical amplification ratios (gain) using a single Nd:YAG laser or with dual pulse laser setups are less than 10 times. The gain of the dual Nd:YAG system that is used to achieve a stand off of 20 meters never exceeded 10, and fewer peaks were observed over background noise. In those instances when no apparent emission peak was observed using the signal generated by a Nd:YAG source for the spark plasma, the amplification ratio reported for the carbon dioxide laser amplification is obtained by comparing the intensity in counts (AU) to the background noise of the signal captured using the Nd:YAG laser alone. In these cases, the actual ratio may be substantially greater than that shown in FIG. 9, but the actual amplification cannot be determined, because the intensity of the signal cannot be resolved from the background noise. In FIG. 10, a comparison is made between a standard LIBS signal and the experimental TEPS signal captured using the system shown in FIGS. 4 and 5. FIGS. 11A and 11B shows two different time delays for emission of a pulse from the carbon dioxide laser in relation to the pulse emitted by the Nd:YAG laser in the experimental setup of FIGS. 4 and 5. As previously discussed, the time delay selected is significant in the amplification of the signal detected.

In one example, optical elements may be used to align the locations of two or more laser beams without aligning the lasers themselves. For example, the laser beams may be dynamically aligned to provide at least a nominal emission spectra from a target surface located at a distance from the system. The system may be combined with a laser range finder, directional control of the laser beams, and other devices to test a plurality of targets without moving the lasers, for example, such as illustrated in FIGS. 1-3, for example.

In one example, a plurality of targets are tested in less than one minute. For example, one hundred targets at different locations may be tested in less than one minute using a laser range finder and optics for providing directional alignment of the laser beam, such as illustrated in the system illustrated in FIG. 3. Alternatively, microtesting may survey many samples from a single surface of a target.

In one example, the TEPS system can function as one subsystem along with multiple other laser spectroscopy subsystems, such as a Raman Spectroscopy subsystem, where the combination of multiple laser spectroscopy subsystems may provide better target discrimination, range, and reduced false alarm rate when combined using appropriate data fusion algorithms and chemometrics. The laser systems illustrated in FIGS. 2 and 3 may provide information from both TEPS and RAMAN spectroscopes. In the example of FIG. 3, a separate detector using a diffraction grating is arranged as a RAMAN spectroscope for detecting signals generated using the lasers common to the TEPS. In one example, both RAMAN spectroscopy and TEPS are conducted using the system illustrated in FIG. 3, and the captured signal data is combined and analyzed to determine a characteristic signature of trace elements of an explosive, such as Cemex, C4, or nitroglycerin. For example, a YAG beam may be used at its frequency-shifted, eye-safe wavelength and power for generating either simultaneously or serially emissions for analysis by the RAMAN spectroscope and the TEPS spectroscope(s).

In one example, illustrated schematically in FIG. 12, the TEPS/RAMAN spectroscopy system 1200 is housed in a airport baggage conveyor system, including a blast shield 1210, a system of conveyor belts 1230, and controls 1240, which are illustrated schematically. The spectroscopy system 1200 is used to scan articles 1201, 1202, 1203 passing through the baggage conveyor system using both TEPS and RAMAN from a distance L, using the same lasers and optics for both the TEPS and RAMAN systems. For example, the distance L may he from one to five meters, for example. If a harmful or explosive residue is detected, then the conveyor 1230 may be stopped by the controls 1240, with the bag in a safe region of the conveyor system protected by a blast shield 1210, or the bag may be redirected B to a safe holding area (not shown) by the conveyor system 1230, for example. In one example, the spectroscopy system may be mechanically or optically controlled for directing A the laser beams 1220 to detect multiple locations on a single article or to redirect the beams to multiple articles being displaced along the conveyor 1230. For example, the spectroscopy system 1200 may be of the type illustrated in FIG. 3.

Figure 13:
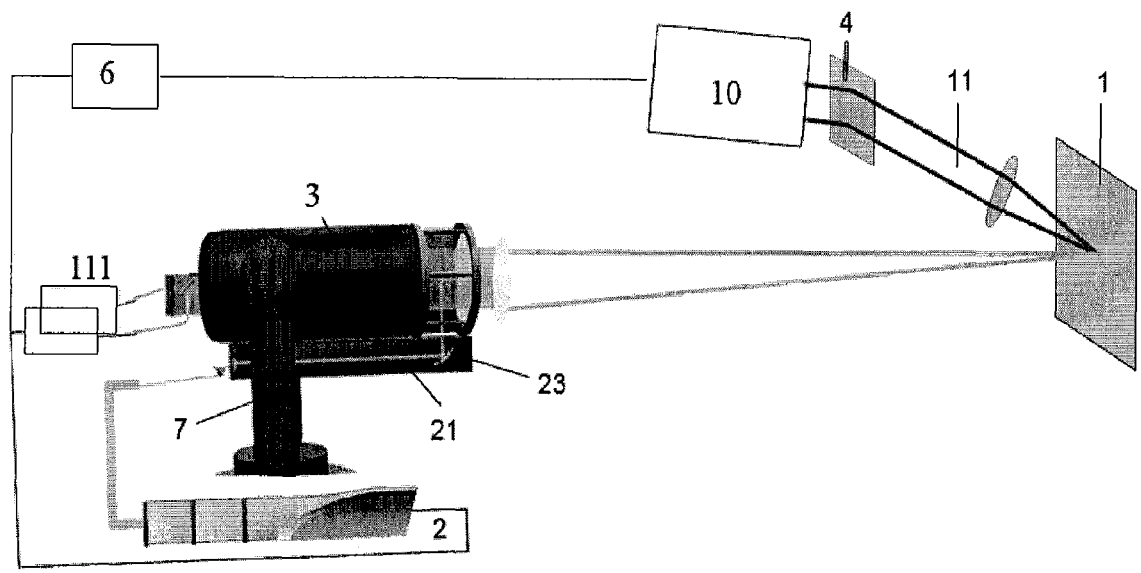
FIG. 13 schematically illustrates one example of a stand off plasma laser spectroscopy system using a telescope mounted on an adjustable mount.

In FIG. 13, a schematic illustration is provided of a standoff laser induced plasma spectroscope comprising spectroscopes 111, a Nd:YAG frequency-shifted laser 2 having a characteristic wavelength of an output beam 21 of about 266 nanometers redirected by optical elements 23 to be focused by a telescope 3 mounted on an isolated, multidirectional mount 7, which is automatically aligned with the output beam 11 of a carbon dioxide laser 10, which is directed by optical elements 4, such that the output beams 11, 21 are focused on or about a surface of a target 5. A controller 6 controls the timing of the delays in generating a pulse for each of the output beams 11, 21 and detection by the spectroscopes 111. In this example, the optics of the carbon dioxide laser must be of a different type than the optics of the Nd:YAG laser and must be capable of redirecting the 10,600 nanometer wavelength of the output beam 11 of the carbon dioxide laser in order to direct the beam to the target surface. For the purpose of this experiment, the carbon dioxide laser and its optics were located close to the target, but the Nd:YAG laser and spectroscopes were disposed at a distance of 15 meters to 70 meters from the target. The Nd:YAG laser uses the optics of a telescope to focus the frequency-shifted output beam 21 to a high density, in order to initiate a spark plasma on the surface of the target 5. The optics of the telescope 3 may be used to collect emission signals from the cooling plasma for the spectroscopes, also, for example.

Figure 14A:
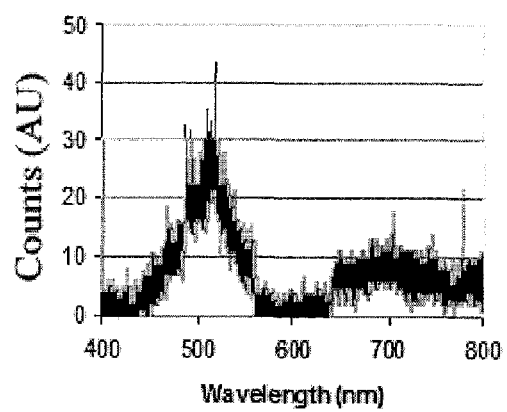
FIGS. 14A and 14B illustrate a LIBS spectra for a clean ceramic surface using (14A) LIBS and (14B) a TEPS incorporating a carbon dioxide laser at a stand off distance of 15 meters.
Figure 14B:
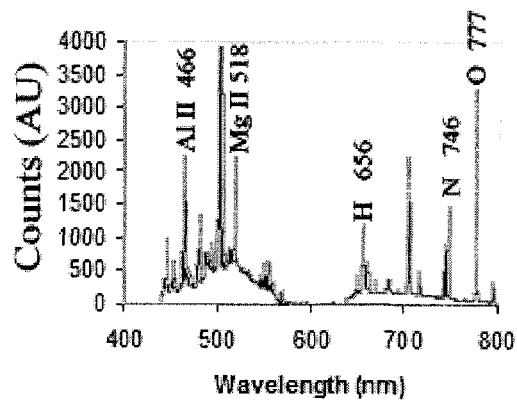

FIGS. 14A and 14B illustrate a LIBS spectra for a clean ceramic surface using (14A) LIBS and (14B) TEPS at a stand off distance of 15 meters. The peak for nitrogen (764 nanometers) has a gain of 250×, while the peak for oxygen (777 nanometers) has a gain of 300×, which is not substantially changed from the gain detected when a wavelength of 1064 nanometers was used in a laboratory bench experiment.

Figure 15A:
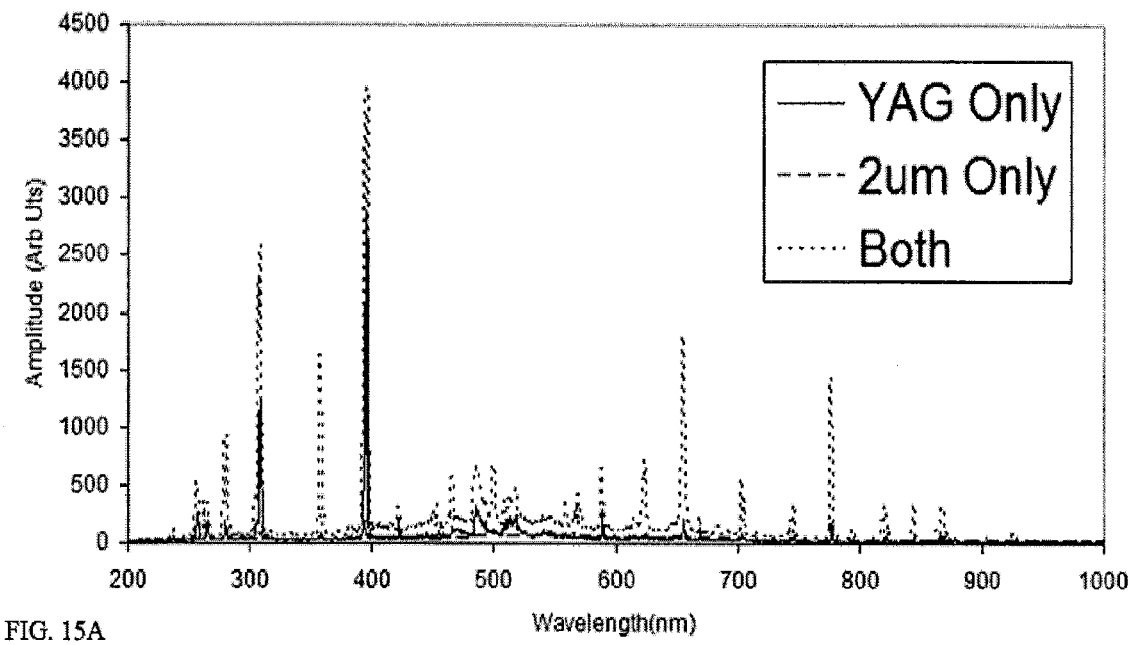
FIG. 15A graphically illustrates the measured signals for a 1064 nanometer Nd:YAG laser, a 2000 nanometer infrared laser, and a combination of both of the lasers on a ceramic substrate.
Figure 15B:
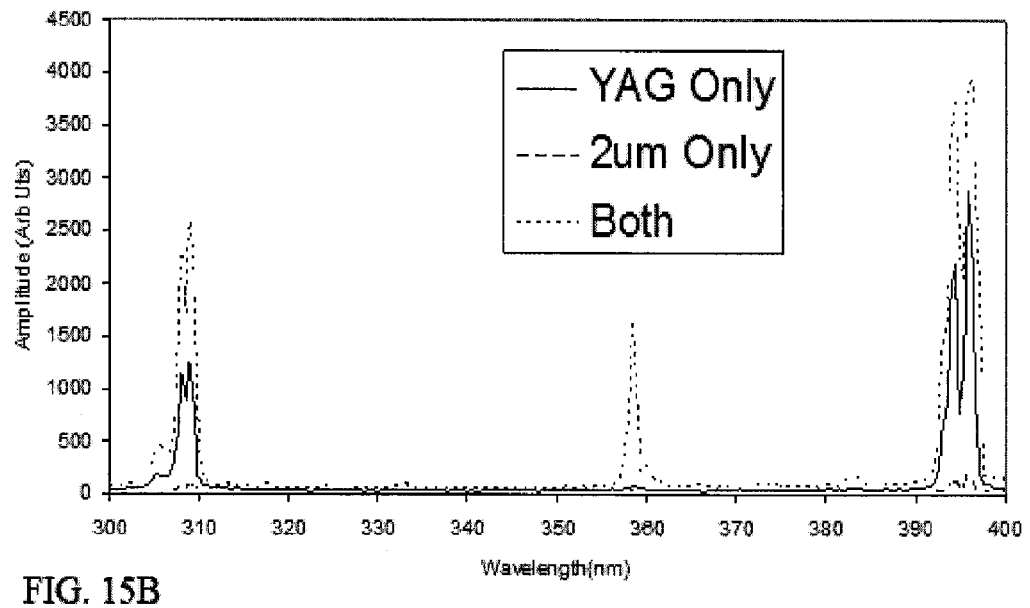
FIG. 15B graphically illustrates a portion of the wavelengths measured to more clearly show the difference between the amplitude detected by the spectroscopes with and without amplification by a 2 micrometer laser beam. \

FIG. 15 graphically illustrates the measured signals for a 1064 nanometer Nd:YAG laser, a 2000 nanometer infrared laser, and a combination of both of the lasers on a ceramic substrate. The 2000 nanometer infrared laser has a pulse width at half maximum of only 10 nanoseconds, which is much shorter than the 100 nanosecond pulse width at half maximum of the carbon dioxide laser used in TEPS. In this example, the lasers were aligned on a benchtop to determine if the 2000 nanometer infrared laser would achieve similar gain, as observed for the carbon dioxide laser. The beam of the 2000 nanometer laser is characterized by a power of 25 milliJoules and a spot diameter of about 2 millimeters. A gain of 3× to 10× is observed for certain of the signal peaks for the combination of both of the lasers compared to the Nd:YAG laser, alone, which is much less than the gain obtained using a carbon dioxide laser. Indeed, the gain observed is about the same as measured using two Nd:YAG lasers, each having 1064 nanometer wavelengths. The interpulse delay exhibited a plateau from 3 to 10 nanoseconds, which is similar to results for dual pulse LIBS. The carbon dioxide laser exhibited its maximum peak amplification at an interpulse delay of only about 0.5 to 1.5 nanoseconds. The beam diameter, output power or pulse width of the 2000 nanometer solid state laser source may be insufficient to reach its maximum amplification potential. Other differences between this experiment and the experiment using a carbon dioxide laser were the wavelength (10,600 nanometers for CO2 laser compared to 2000 nanometers) and the pulse width (100 nanoseconds for the CO2 laser compared to 10 nanoseconds).

In another example, the same infrared laser source was used at a frequency shifted wavelength of 5000 nanometers. The power of the infrared laser source was less than 5 milliJoules with a 10 nanosecond pulse width, and a spot size of 200 microns. No gain was detected using this infrared laser source with a single pulse LIBS setup with a Nd:YAG spark pulse laser source at 1064 nanometers, 50 milliJoules, and a 5 nanosecond pulse width. Thus, the power and spot size were insufficient to initiate a substantially amplification of the plasma.

Figure 16A:
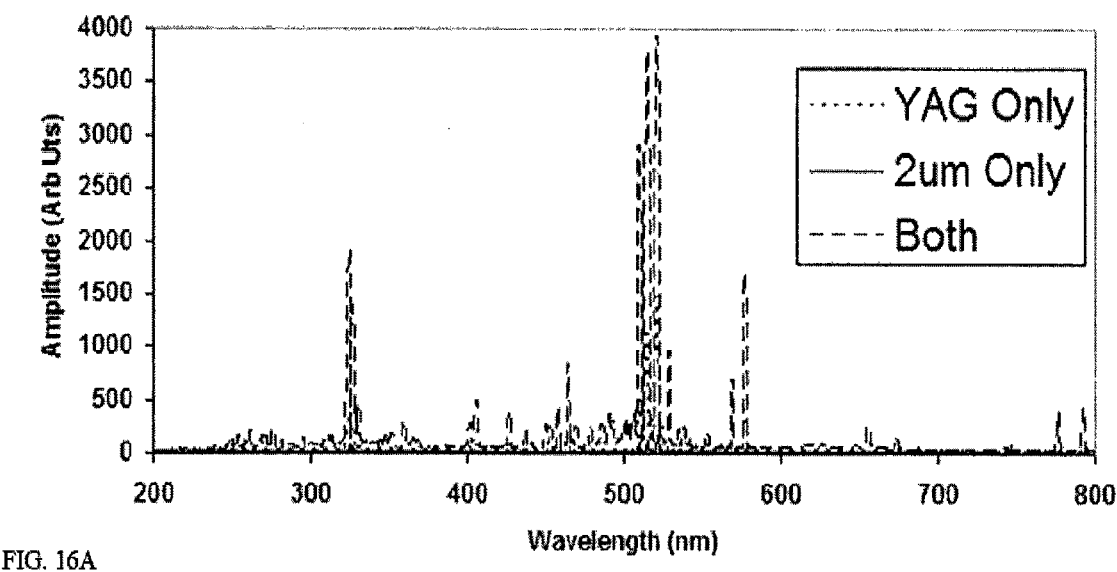
FIG. 16A graphically illustrates the measured signals for a 1064 nanometer Nd:YAG laser, a 2000 nanometer infrared laser, and a combination of both of the lasers on a copper substrate.
Figure 16B:
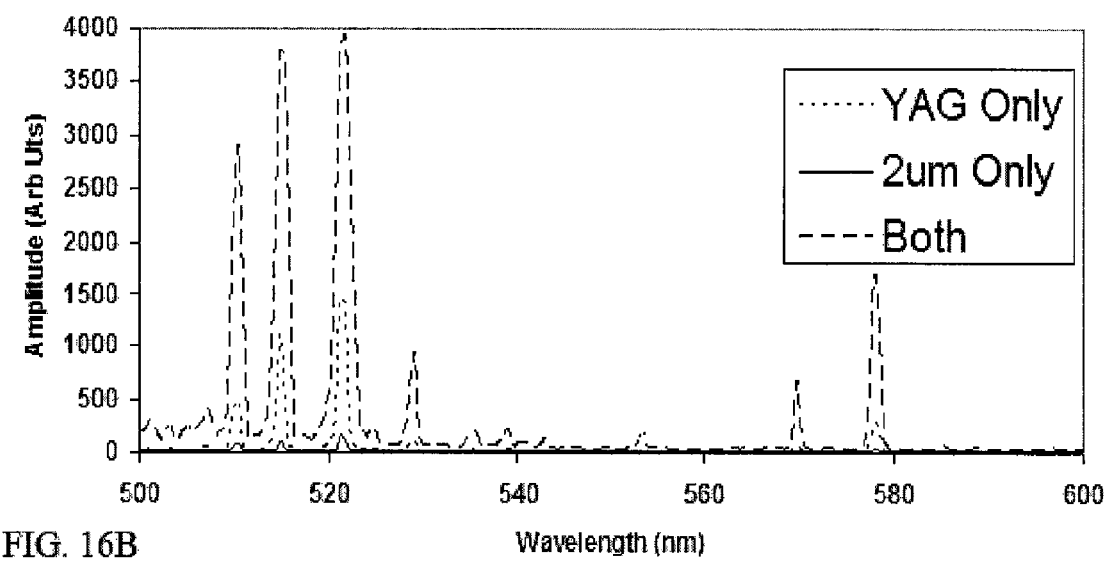
FIG. 16B graphically illustrates a portion of the wavelengths shown in FIG. 16A for clarity.

FIG. 16 graphically illustrates the same experimental setup as in FIG. 15, except that the substrate is a copper substrate. Using this substrate a gain for some of the emission lines is observed in a range from 5× to 30×, which is still much less than gain observed using a carbon dioxide laser.

Figure 17:
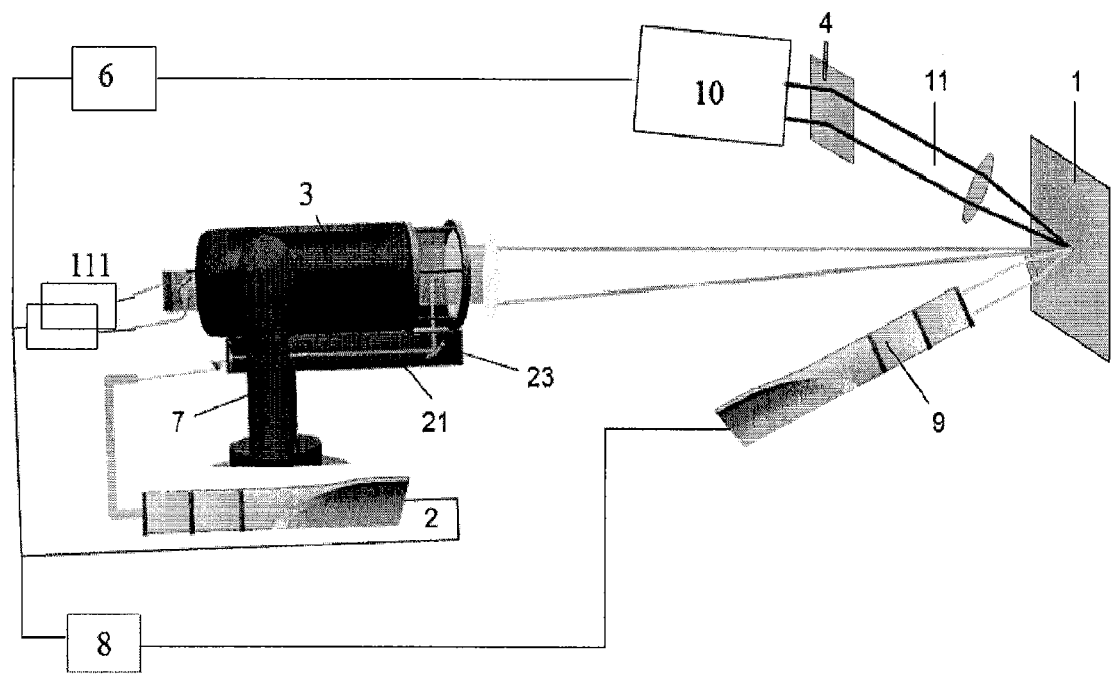
FIG. 17 illustrates an example of a laser induced plasma spectroscopy system.
Figure 18:
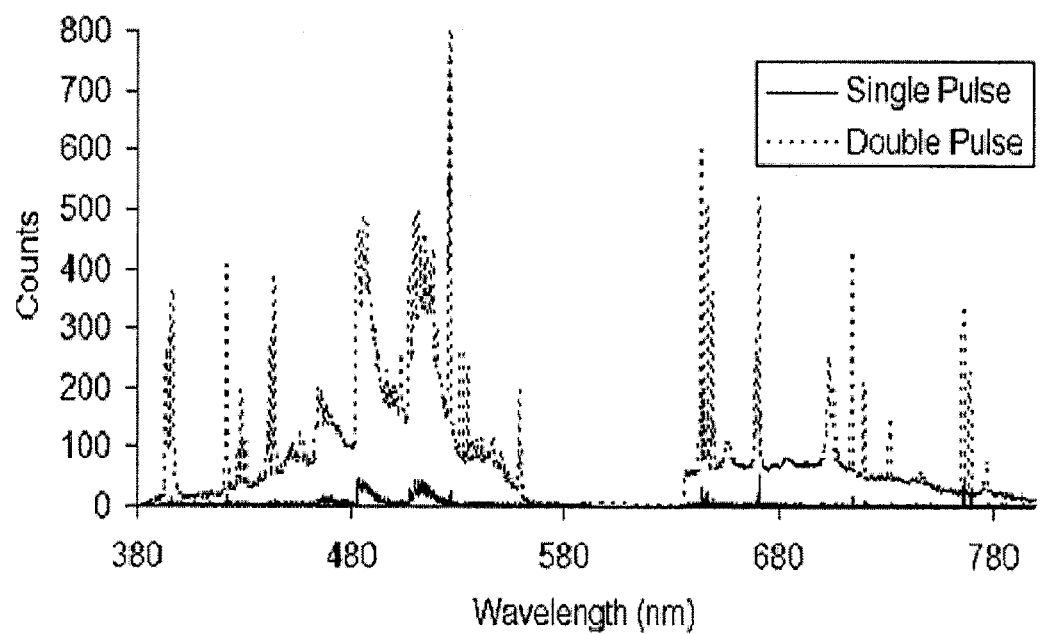
FIG. 18 graphically compares emissions detected using a single pulse from a Nd:YAG laser with a double pulse laser induced plasma and a 4 microsecond delay.
Figure 19:
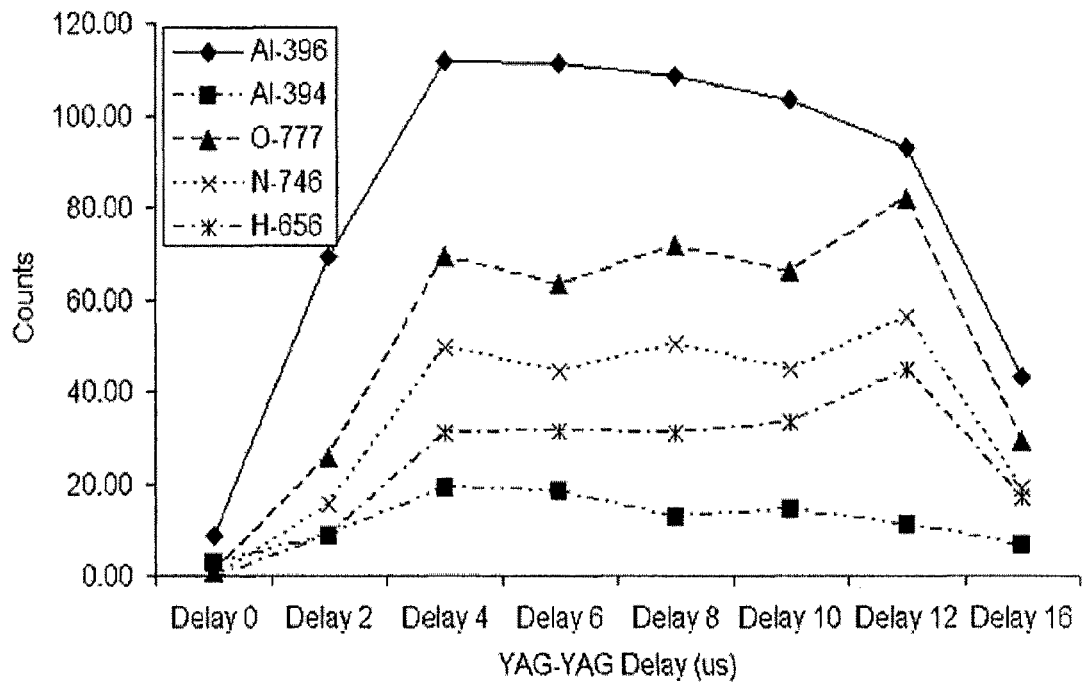
FIG. 19 graphically illustrates an effect on the intensity of several of the peak emissions by selecting the delay between the peak pulse of a first laser and the peak pulse of a second laser.

FIG. 17 illustrates, schematically, a double pulse LIBS setup combined with a carbon dioxide laser. This is similar to the illustration of FIG. 13, except that a second Nd:YAG laser 9 is added for comparing double pulse LIBS to TEPS. A second delay generator 8 controls the delay between the pulsed output of the first. Nd:YAG laser 2 and the second Nd:YAG laser 9. In the data graphically represented in FIG. 18, a delay of 4 microseconds was used between the first Nd:YAG laser 2 and the second Nd:YAG laser 9 (with no pulse from the carbon dioxide laser). FIG. 18 compares a single pulse from the Nd:YAG laser 2 generating the spark plasma with a double pulse LIBS with a 4 microsecond delay. The effect of the delay is illustrated by the data for several peaks graphically illustrated in FIG. 19. A delay of between 4 microseconds and about 12 microseconds has substantially the same effect on the gain compared to a single pulse LIBS.

Figure 20:
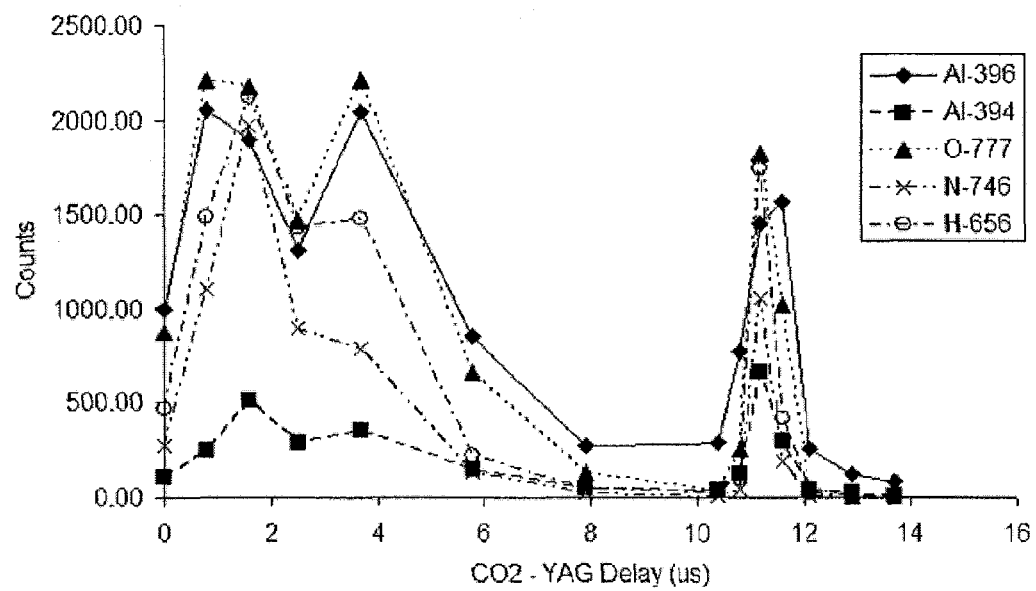
FIG. 20 illustrates an effect on the intensity of several of the peak emissions by selecting the delay between the carbon dioxide laser and the first Nd:YAG laser in a combination of a dual pulse LIBS and TEPS, as illustrated in the arrangement of FIG. 17, for example.
Figure 20:
Figure 21:
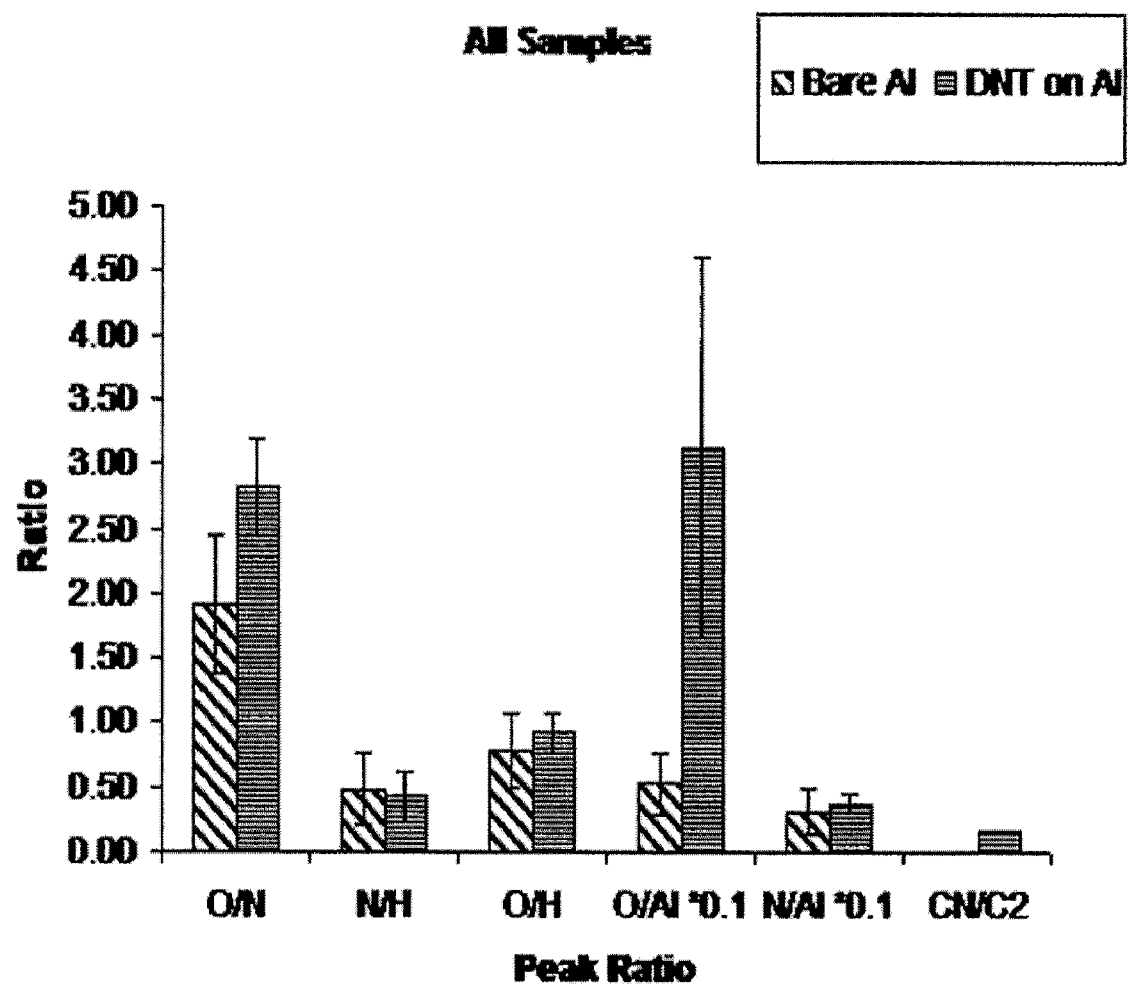
FIG. 21 illustrates results of tests on a bare aluminum target compared to a target having an aluminum surface contaminated with DNT residue for one particular delay time selected for the carbon dioxide laser and the second Nd:YAG laser, as illustrated in the arrangement of FIG. 17, for example.
Figure 22:
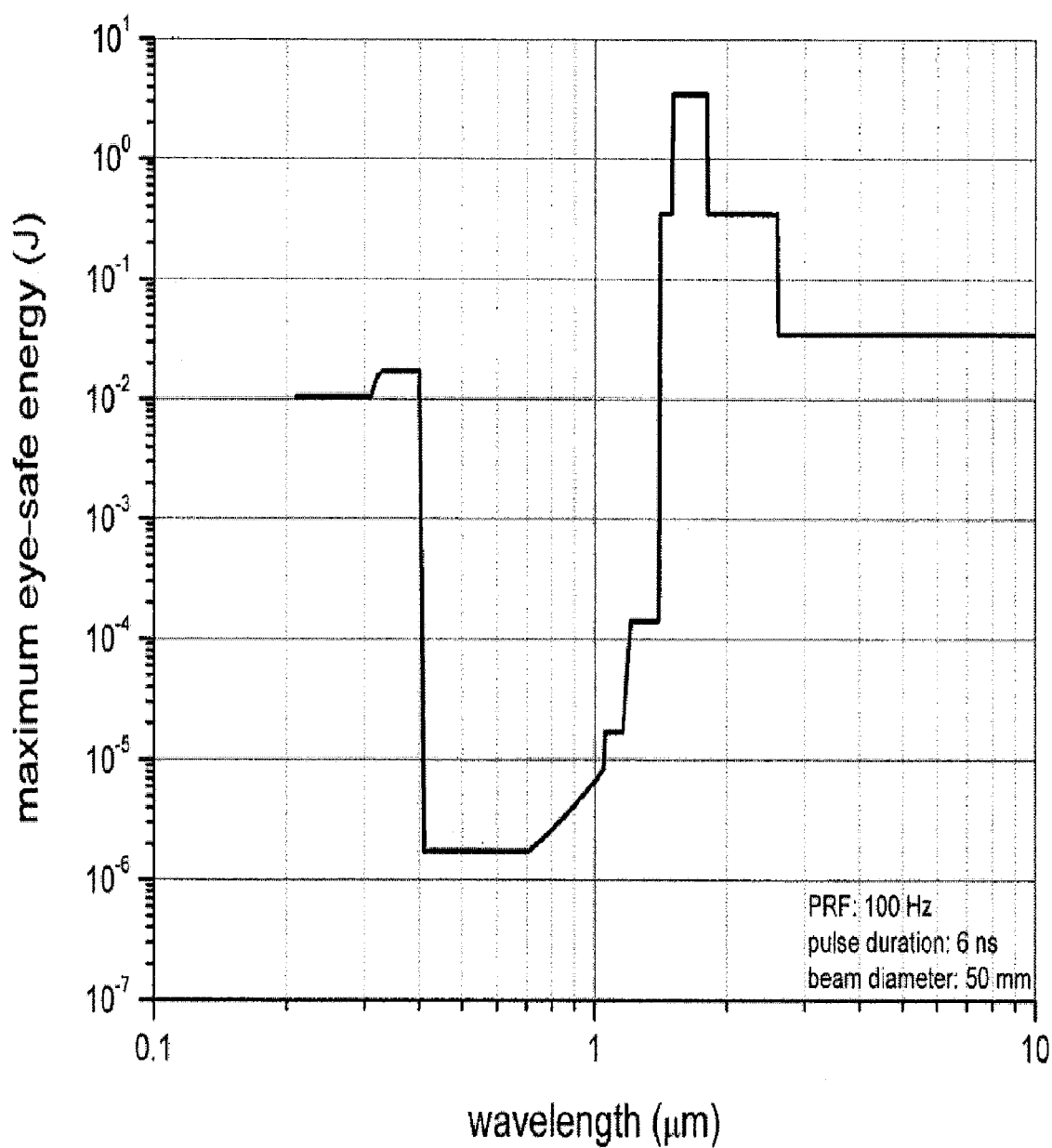
FIG. 22 illustrates a graph of eye safe power for a 50 millimeter diameter beam at various wavelengths.

FIG. 20 graphically illustrates the signal detected for several peaks when double pulse LIBS is combined with the emission of a pulse from a carbon dioxide laser in a TEPS. In the experiment illustrated by FIG. 20, the delay between the first Nd:YAG laser 2 and the second Nd:YAG laser 9 was 10 microseconds, as illustrated in the pulse time line below the graphical results. The delay for the carbon dioxide layer was swept from 0 microseconds to nearly 14 microseconds. As expected, the results for this example of TEPS combined with dual pulse LIBS is virtually identical to FIG. 8 (TEPS only) up to 10 microseconds. Then, the emitting of the second Nd:YAG pulse at 10 microseconds briefly amplifies the plasma, which allows the carbon dioxide laser to amplify the amplified plasma. The amplification of the amplified plasma is highly dependent on the delay offset between the second Nd:YAG laser 9 and the carbon dioxide laser. The maximum gain is measured at a delay offset of about 1 microsecond. The combination of the carbon dioxide pulse and the pulse of the second Nd:YAG laser 9 does not provide for a substantially different gain than that detected for TEPS, alone. Comparing TEPS to TEPS with dual pulse LIBS, there was no significant difference in the differentiation of the oxygen to nitrogen ratio for detection of a DNT explosive material on an aluminum surface. Thus, there appears to be little justification in combining dual pulse LIBS with TEPS. This is graphically illustrated in FIG. 21, which illustrates the signal for bare aluminum compared to an aluminum surface contaminated with DNT residue. A delay for both the second Nd:YAG laser 9 and the carbon dioxide laser of about 10 microseconds was used. It is possible that the substantial amplification of the signal using TEPS merely overwhelms any small contribution to the signal made by the second pulse in dual pulse LIBS.

In one example, a spark may be created with an ultraviolet (UV) laser pulse, which is at a wavelength that has improved eye safety compared to a range of wavelengths from 400 to 1400 nanometers that strictly limit laser output power. A spark plasma is amplified by the Townsend Effect using a carbon-dioxide (CO2) laser, which also operates at a wavelength that is eye safe at the energy used to amplify the signal. This permits a standoff detection device far more eye-safe than the present state of the art in standoff laser spectroscopy systems, especially in defense and national security applications. It has an additional advantage of using a short wavelength (UV) laser pulse, which is particularly beneficial when performing Raman spectroscopy.

In one example, other sensors of all spectral and other data collection regimes may be used to 'cue' a TEPS system or other combination of laser spectroscopy subsystems, to provide a more efficient search area for the laser spectroscopy/TEPS system to examine.

If implemented with a high power carbon dioxide laser, a TEPS system may be used as an active countermeasure, such as jamming an infrared triggering mechanism, a low yield burn, or a high order detonation. A carbon dioxide laser may be used as a far infrared laser rangefinder. Also, a carbon dioxide laser has a gain line at 11,500 nanometers that may be used instead of the gain line at 10,600 nanometers. It is believed, without limiting the invention, that 11,500 may increase the gain of emissions more than use of the 10,600 nanometer gain line, provide that the carbon dioxide laser outputs sufficient power to reach peak gains, and an integrated TEPS reduces the complexity of optical components and parallax of such a long wavelength coupled co-axially with a shorter wavelength laser.

Other variations and modifications of the TEPS system may be recognized by a person of ordinary skill in the art based on the examples and descriptions provided in this specification. The examples described are illustrative and are not intended to limit the scope of any claims. A chemical emissions signature analyzer, which is known in the art, may be coupled to one of the examples to compare detected emission signals to known signals of hazardous substances. This may use a look up table approach for rapid comparison or may use filters and comparators, ratios of peak intensities, multimodal emission spectroscopy, and other known analysis engines to determine the likelihood of a threat.

What is claimed is:

1. A laser induced plasma spectroscopy system for detecting trace elements on a surface of a target at a stand-off distances of at least 20 meters, comprising:
   a first YAG laser having a frequency-shifted, pulsed beam having a wavelength of 266 nanometers;
   a second laser having a pulsed beam, the pulsed beam of the second laser having a peak energy, a wavelength, a pulse width at half maximum, and a spot diameter at the target;
   at least one telescopic focusing optics for focusing of the pulsed beam of the first YAG laser on the surface of the target, wherein the pulsed beam of the first YAG laser is optically coupled to the at least one telescopic optics, such that the beam of the first YAG laser induces a plasma on the surface of the target at the stand-off distance, when the pulsed beam of the first YAG laser is triggered, and the second laser is optically aligned and the pulsed beam of the second laser has the peak energy, the wavelength, the pulse width at half maximum, the wavelength and the spot diameter selected such that the pulsed beam of the second laser stimulates amplified emissions from the plasma generated by the beam of the first YAG laser;

a spectroscope for detecting the amplified emissions; and a time-delay controller for triggering the emission of the pulsed beam of the first YAG laser and controlling the emission of the pulsed beam of the second laser, wherein a delay between triggering of the pulsed beam of the first YAG laser and the emission of the pulsed beam of the second laser is no greater than twelve microseconds, and the time-delay controller activates the spectroscope such that the amplified emissions are detected by the spectroscope, and the pulsed beam of the second laser has the peak energy, the wavelength, the pulse width at half maximum, the wavelength and the spot diameter selected such that the peak intensity of a plurality of peaks in the amplified emissions spectra that are detected by the spectroscope at the stand-off distance are at least three times the intensity of the same peaks if the plasma induced by the first YAG laser is not amplified by the second laser.

2. The spectroscopy system of claim 1, wherein the second laser is a carbon dioxide laser having a wavelength of about 10600 nanometers, and the at least one telescopic focusing optics includes infrared focusing optics optically aligning the pulsed beam of the carbon dioxide laser such that the pulsed beam of the carbon dioxide laser stimulates amplified emissions from the plasma generated by the beam of the first YAG laser.

3. The spectroscopy system of claim 2, wherein the pulsed beam of the carbon dioxide laser has the peak energy, the wavelength, the pulse width at half maximum, the wavelength and the spot diameter selected such that the peak intensity of a plurality of peaks in the amplified emissions spectra that are detected by the spectroscope at the stand-off distance of at least, 20 meters are at least twenty times the intensity of the same peaks if the plasma induced by the first YAG laser is not amplified by the second laser.

4. The spectroscopy system of claim 2, wherein the pulsed beam of the carbon dioxide laser has the peak energy, the wavelength, the pulse width at half maximum, the wavelength and the spot diameter selected such that the peak intensity of a plurality of peaks in the amplified emissions spectra that are detected by the spectroscope at the stand-off distance of at least 20 meters are at least one hundred times the intensity of the same peaks if the plasma induced by the first YAG laser is not amplified by the second laser.

5. The spectroscopy system of claim 2, wherein the time-delay controller controls the emission of the pulsed beam of the second laser, such that the delay between triggering of the pulsed beam of the first YAG laser and the emission of the pulsed beam of the second laser is no greater than three microseconds.

6. The spectroscopy system of claim 5, wherein the delay is no greater than one microsecond.

7. The spectroscopy system of claim 5, further comprising a RAMAN spectroscope for detecting RAMAN emissions induced by the first YAG laser, the second laser or both the first YAG laser and the second laser.

8. A rapid-fire stand-off detection system, comprising the spectroscopy system of claim 1, and the time-delay controller is coupled to a laser aiming controller such that the system detects the spectra of at least thirty amplified emissions per minute.

9. The system of claim 8, wherein the system detects the spectra of at least three hundred amplified emission per minute.

10. A Townsend Effect Plasma Spectroscopy system, comprising the spectroscopy system of claim 1, wherein the pulse width of the beam of the carbon dioxide laser is about 100 nanoseconds.

11. A detection system for screening articles having a detection surface, comprising the spectroscopy system of claim 1, a conveyor belt, and a detector for determining when one of the articles is present in the range of the spectroscopy system of claim 1, a range finder for determining the distance to the detection surface of the one of the articles that is present in the range of the spectroscopy system of claim 1, and wherein the at least one telescopic focusing optics adjusts the focal length of the pulsed beam of the first YAG laser, such that the beam of the first YAG laser induces a plasma on the surface of the target at the stand-off distance, when the pulsed beam of the first YAG laser is triggered.

12. The system of claim 11, wherein the second laser is a carbon dioxide laser, and the carbon dioxide laser is aligned using optics for aligning an infrared beam of the carbon dioxide laser such that the peak intensity of a plurality of peaks in the amplified emissions spectra that are detected by the spectroscope at the stand-off distance are at least fifty times the intensity of the same peaks if the plasma induced by the first YAG laser is not amplified by the pulsed beam of the carbon dioxide laser.

13. A Townsend Effect Plasma Spectroscopy system, comprising:

a first laser having a pulsed beam;

a carbon dioxide laser having a pulsed beam, the pulsed beam of the carbon dioxide laser having a peak energy, a wavelength, a pulse width at half maximum, and a spot diameter at the target;

at least one telescopic focusing optics for focusing of the pulsed beam of the first laser, wherein the pulsed beam of the first laser is optically coupled to the at least one telescopic optics, such that the beam of the first laser induces a plasma, when the pulsed beam of the first laser is triggered, and the carbon dioxide laser is optically aligned and the pulsed beam of the carbon dioxide laser has the peak energy, the wavelength, the pulse width at half maximum, and the spot diameter selected such that the pulsed beam of the carbon dioxide laser stimulates amplified emissions from the plasma generated by the beam of the first laser;

a spectroscope for detecting the amplified emissions; and a time-delay controller for triggering the emission of the pulsed beam of the first laser and controlling the emission of the pulsed beam of the carbon dioxide laser, wherein a delay between triggering of the pulsed beam of the first laser and the emission of the pulsed beam of the second laser is no greater than three microseconds, and the time-delay controller activates the spectroscope such that the amplified emissions are detected by spectroscope, and the pulsed beam of the carbon dioxide laser has the peak energy, the wavelength, the pulse width at half maximum, the wavelength and the spot diameter selected such that the peak intensity of a plurality of peaks in the amplified emissions spectra that are detected by the spectroscope are at least ten times the intensity of the same peaks if the plasma induced by the first laser is not amplified by the carbon dioxide laser.

14. The Spectroscopy system of claim 13, wherein the pulsed beam of the carbon dioxide laser has the peak energy, the wavelength, the pulse width at half maximum, the wavelength and the spot diameter selected such that the peak intensity of a plurality of peaks in the amplified emissions spectra that are detected by the spectroscope are at least fifty times the intensity of the same peaks if the plasma induced by the first laser is not amplified by the carbon dioxide laser.

15. The Spectroscopy system of claim 13, further comprising a laser range finder for determining the distance to a detection surface, and a focusing controller for adjusting a focal length of the pulsed beam of the first laser, such that the at least one telescopic optics focuses the pulsed beam of the first laser on the detection surface.

16. The Spectroscopy system of claim 15, further comprising a laser aiming controller, the laser aiming controller, the laser range finder, the at least one telescopic optics and the time-delay controller being coupled such that the first laser induces a plasma at the detection surface when the pulsed beam of the first laser triggers the first laser.

17. The Spectroscopy system of claim 16, wherein the laser aiming controller is coupled to a video terminal and an input device, such that, when an operator selects the detection surface using the input device, the laser aiming controller adjusts the direction of the pulsed beam of the first laser and the pulsed beam of the carbon dioxide laser, the laser range finder measures the distance to the detection surface, the at least one telescopic optics adjusts the focal length of the first laser such that the pulsed beam of the first laser induces the plasma at the detection surface when the first laser is triggered by the time-delay controller.

18. A remote controlled mobile device, comprising the Spectroscopy system of claim 17, a drive unit and a directional controller, such that the input device is capable of directing movement of the mobile device to within an operating range of the Spectroscopy system for detecting trace elements on the detection surface.

19. The remote controlled mobile device of claim 18, wherein the Spectroscopy system further comprises a RAMAN spectroscope, and the first laser, the carbon dioxide laser or both thereof are triggered by the time-delay controller for inducing emissions detectable by the RAMAN spectroscope.

20. The remote controlled mobile device of claim 19, wherein a look up table of laser-induced plasma spectroscopy and RAMAN spectroscopy signatures are provided for comparison to emissions detected, such that specific threats are identified.

21. The remote controlled mobile device of claim 20, wherein at least a portion of the look up table is updated using secure communications.

22. A laser spectroscopy system, comprising:
a telescope;
a first laser having annularly aligned laser output annularly aligned along the axis of the telescope, when the annularly aligned laser output of the first laser is emitted;
a second laser having an axial laser output aligned along the axis of the telescope, when the axial aligned laser output of the second laser is emitted;
a delay generator or delay controller capable of coupling the timing of emissions of the annularly aligner laser output of the first laser and the axial aligned laser output of the second laser during controlled emission of the first laser and the second laser;
a beam director comprising optical elements for coupling the focus of the annularly aligned laser output of the first laser and the axial aligned laser output of the second laser and a common output port for both the annularly aligned laser output of the first laser and the axial aligned laser output of the second laser;
a mounting system capable of aiming the beam director;
wherein the first laser or the second laser has a power density capable of initiating a spark plasma and both the first laser and the second laser have an operationally eye safe wavelength, power and beam divergence during use in a field environment;
at least one spectroscope for detecting emissions generated by the first laser, the second laser or a combination of the first laser and the second laser; wherein emission of a laser output of the first laser and emission of a laser output of the second laser are delayed by the delay generator or the delay controller such that the delay between the emission of the laser output from the first laser and the emission of the laser output from the second laser is no greater than twelve microseconds; wherein the at least one spectroscope includes a plurality of spectroscopes, including a laser induced plasma spectroscope for detecting amplified emissions and a RAMAN spectroscope such that a spectra of the RAMAN spectroscope, a spectra of the laser induced plasma spectroscope or both thereof are comparable to known signatures of spectra of compounds by the laser spectroscopy system.

* * * * *